(12) United States Patent
MacLean et al.

(10) Patent No.: US 9,840,705 B2
(45) Date of Patent: Dec. 12, 2017

(54) MATERIALS AND METHODS FOR TREATMENT OF PULMONARY ARTERIAL HYPERTENSION

(71) Applicant: THE UNIVERSITY COURT OF THE UNIVERSITY OF GLASGOW, Glasgow (GB)

(72) Inventors: Margaret R. MacLean, Glasgow (GB); Emma Wallace, Glasgow (GB); Andrew H. Baker, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 0 days.

(21) Appl. No.: 15/100,638

(22) PCT Filed: Dec. 1, 2014

(86) PCT No.: PCT/GB2014/053566
§ 371 (c)(1),
(2) Date: Jun. 1, 2016

(87) PCT Pub. No.: WO2015/082896
PCT Pub. Date: Jun. 11, 2015

(65) Prior Publication Data
US 2016/0304869 A1    Oct. 20, 2016

(30) Foreign Application Priority Data

Dec. 2, 2013 (GB) .................................. 1321237.8
Sep. 19, 2014 (GB) .................................. 1416570.8

(51) Int. Cl.
| | |
|---|---|
| *A61K 31/70* | (2006.01) |
| *C07H 21/02* | (2006.01) |
| *C07H 21/04* | (2006.01) |
| *C12N 15/113* | (2010.01) |
| *C12N 7/00* | (2006.01) |
| *C12N 5/00* | (2006.01) |

(52) U.S. Cl.
CPC .............. *C12N 15/113* (2013.01); *C12N 7/00* (2013.01); *C12N 2310/141* (2013.01); *C12N 2320/30* (2013.01); *C12N 2740/15041* (2013.01)

(58) Field of Classification Search
None
See application file for complete search history.

(56) References Cited

U.S. PATENT DOCUMENTS

2009/0281167 A1* 11/2009 Shen .................... C12N 15/113
514/44 A

FOREIGN PATENT DOCUMENTS

WO    2009137807 A2    11/2009
WO    2011088309 A1    7/2011

OTHER PUBLICATIONS

Austin, ED. et al. T lymphocyte subset abnormalities in the blood and lung in pulmonary arterial hypertension. Respir Med Mar. 2010;104(3) :454-62.
Bouchie, A. First microRNA mimic enters clinic. Nat Biotechnol Jul. 9, 2013;31(7):577.
Caruso, P. et al. Dynamic Changes in Lung MicroRNA Profiles During the Development of Pulmonary Hypertension due to Chronic Hypoxia and Monocrotaline. Arteriosclerosis Thrombosis and Vascular Biology Apr. 2010;30(4) :716-U182.
Caruso, P. et al. A Role for miR-145 in Pulmonary Arterial Hypertension / Novelty and Significance. Circ Res Jul. 20, 2012;111(3) :290-300.
Dempsie, Y. et al. Converging evidence in support of the serotonin hypothesis of dexfenfluramine-induced pulmonary hypertension with novel transgenic mice. Circulation Jun. 3, 2008;117(22) :2928-37.
Dempsie, Y. et al. Development of pulmonary arterial hypertension in mice over-expressing S100A4/Mts1 is specific to females. Respiratory Research 2011;12(1):159.
Dempsie, Y. et al. Dexfenfluramine and the oestrogen-metabolizing enzyme CYP1BI in the development of pulmonary arterial hypertension. Cardiovasc Res Jul. 1, 2013;99(1) :24-34.
Grant, J. et al. MicroRNAs in pulmonary arterial remodeling. Cell Mol Life Sci 2013;1-16.
Keegan, A. et al. Contribution of the 5-HT1B receptor to hypoxia-induced pulmonary hypertension converging evidence using 5-HT1B-receptor knockout mice and the 5-HT1B/1D-receptor antagonist GR127935. Circulation Research, vol. 89, No. 12, Dec. 7, 2001, pp. 1231-1239.
Lane, KB et al. Heterozygous germline mutations in BMPR2, encoding a TGF-beta receptor, cause familial primary pulmonary hypertension. Nature Genetics Sep. 2000; 26 (1): 81-4.
Lawrie, A. et al. Interdependent serotonin transporter and receptor pathways regulate S100A4/Mts1, a gene associated with pulmonary vascular disease. Circ Res Aug. 5, 2005;97 (3) :227-35.
MacIntyre, PD. et al. Effect of Subcutaneous Sumatriptan, A Selective 5Htl1 Agonist, on the Systemic, Pulmonary, and Coronary Circulation. Circulation Feb. 1993;87 (2) :401-5.
MacLean, MR. et al. Evidence for 5-HT1-like receptor-mediated vasoconstriction in human pulmonary artery. British Journal of Pharmacology Sep. 1996;119(2) :277-82.
MacLean, MR. et al. Increased contractile response to 5-hydroxytryptamine(1)-receptor stimulation in pulmonary arteries from chronic hypoxic rats: role of pharmacological synergy. British Journal of Pharmacology Oct. 2001; 134 (3): 614-20.
MacLean, MR. et al. Overexpression of the 5-hydroxytryptamine transporter gene—Effect on pulmonary hemodynamics and hypoxia-induced pulmonary hypertension. Circulation May 4, 2004;109(17) :2150-5.
Mair, KM. et al. Novel interactions between the 5-HT transporter, 5-HT(1B) receptors and Rho kinase in vivo and in pulmonary fibroblasts. British Journal of Pharmacology Oct. 2008; 155 (4): 606-16.

(Continued)

*Primary Examiner* — Sean McGarry
(74) *Attorney, Agent, or Firm* — FisherBroyles, LLP; Victoria L. Boyd

(57) ABSTRACT

The invention relates to the use of microRNA 96 and precursors and mimics thereof for the inhibition of vascular cell proliferation and/or vascular remodelling, and for the treatment of associated medical conditions such as pulmonary arterial hypertension (PAH).

20 Claims, 10 Drawing Sheets

(56) References Cited

OTHER PUBLICATIONS

Millan, Mark J. MicroRNA in the regulation and expression of serotonergic transmission in the brain and other tissues. Current Opinion in Pharmacology, vol. 11, No. 1, 2011, pp. 11-22.
Morecroft, I. et al. Effect of Tryptophan Hydroxylase 1 Deficiency on the Development of Hypoxia-Induced Pulmonary Hypertension. Hypertension Jan. 1, 2007;49(1) :232-6.
Morecroft, I. et al. Gene Therapy by Targeted Adenovirus-mediated Knockdown of Pulmonary Endothelial Tph1 Attenuates Hypoxia-induced Pulmonary Hypertension. Mol Ther Aug. 2012; 20(8) :1516-28.
Morecroft, I. et al. 5-hydroxytryptamine receptors mediating contraction in human small muscular pulmonary arteries: importance of the 5-HT1B receptor. British Journal of Pharmacology Oct. 1999; 128 (3): 730-4.
Morecroft, I. et al. Functional interactions between 5-hydroxytryptamine receptors and the serotonin transporter in pulmonary arteries. J Pharmacol Exp Ther May 2005;313(2) :539-48.
Morecroft, I. et al. In vivo effects of a combined 5-HT(1B) receptor/ SERT antagonist in experimental pulmonary hypertension. Cardiovasc Res Feb. 2010 1;85(3) :593-603.
Savai, R. et al. Immune and inflammatory cell involvement in the pathology of idiopathic pulmonary arterial hypertension. Am J Respir Crit Care Med Nov. 1, 2012;186(9) :897-908.
Seuwen, K. et al. Serotonin stimulates DNA synthesis in fibroblasts acting through 5-HT1B receptors coupled to a Gi-protein. Nature Sep. 15, 1988;335(6187) :254-6.
Shapiro, S. et al. Sex differences in the diagnosis, treatment, and outcome of patients with pulmonary arterial hypertension enrolled in the registry to evaluate early and long-term pulmonary arterial hypertension disease management. Chest Feb. 2012;141(2) :363-73.
Stefulj, J. et al. mRNA expression of serotonin receptors in cells of the immune tissues of the rat. Brain Behav Immun Sep. 2000; 14 (3) :219-24.
White, K. et al. The serotonin transporter, gender, and 17 beta oestradiol in the development of pulmonary arterial hypertension. Cardiovasc Res May 2011;90(2) :373-82.
White, K. et al. Serotonin transporter, sex, and hypoxia: microarray analysis in the pulmonary arteries of mice identifies genes with relevance to human PAH. Physiological Genomics Apr. 2011; 43 ( 8 ): 417-37.
Yang, GB. et al. Expression of mRNA for multiple serotonin (5-HT) receptor types/subtypes by the peripheral blood mononuclear cells of rhesus macaques. J Neuroimmunol Sep. 2006;178(1-2) :24-9.
Yin, J. et al. 5-HT1B receptors play a prominent role in the proliferation of Tlymphocytes. Journal of Neuroimmunology Dec. 2006;181(1-2) :68-81.
Jensen, KP et al. (2009) A common polymorphism in serotonin receptor 1B mRNA moderates regulation by miR-96 and associates with aggressive human behaviors. Molecular Psychiatry 14:381-389.
MacLean and Morecroft (2001) Increased contractile response to 5-hydroxytryptamine1-receptor stimulation in pulmonary arteries from chronic hypoxic rats: role of pharmacological synergy. Br. J. Pharm. 134:614-620.
MacLean, MR. et al. (1996) 5-Hydroxytryptamine receptors mediating vasoconstriction in pulmonary arteries from control and pulmonary hypertensive rats. Br. J. Pharm. 119:917-930.
MacLean, MR. et al. (1993) Adverse reactions associated with sumatriptan. Lancet 341:1092.
Morecroft and MacLean (1998) 5-Hydroxytryptamine receptors mediating vasoconstriction and vasodilation in perinatal and adult rabbit small pulmonary arteries. Br. J. Pharm. 125:69-78.
Murdoch R. et al. (2003) 5-HT moduline: an endogenous inhibitor of 5-HT1B/1D-mediated contraction in pulmonary arteries. Br. J. Pharm. 138:795-800.
Trang, P et al. (2011) Systemic Delivery of Tumor Suppressor microRNA Mimics Using a Neutral Lipid Emulsion Inhibits Lung Tumors in Mice. Molecular Therapy 19(6):1116-1122.
West, J et al. (2008) Mice expressing BMPR2R899X transgene in smooth muscle develop pulmonary vascular lesions. Am J Physiol Lung Cell Mol Physiol 295:L744-L755.

\* cited by examiner

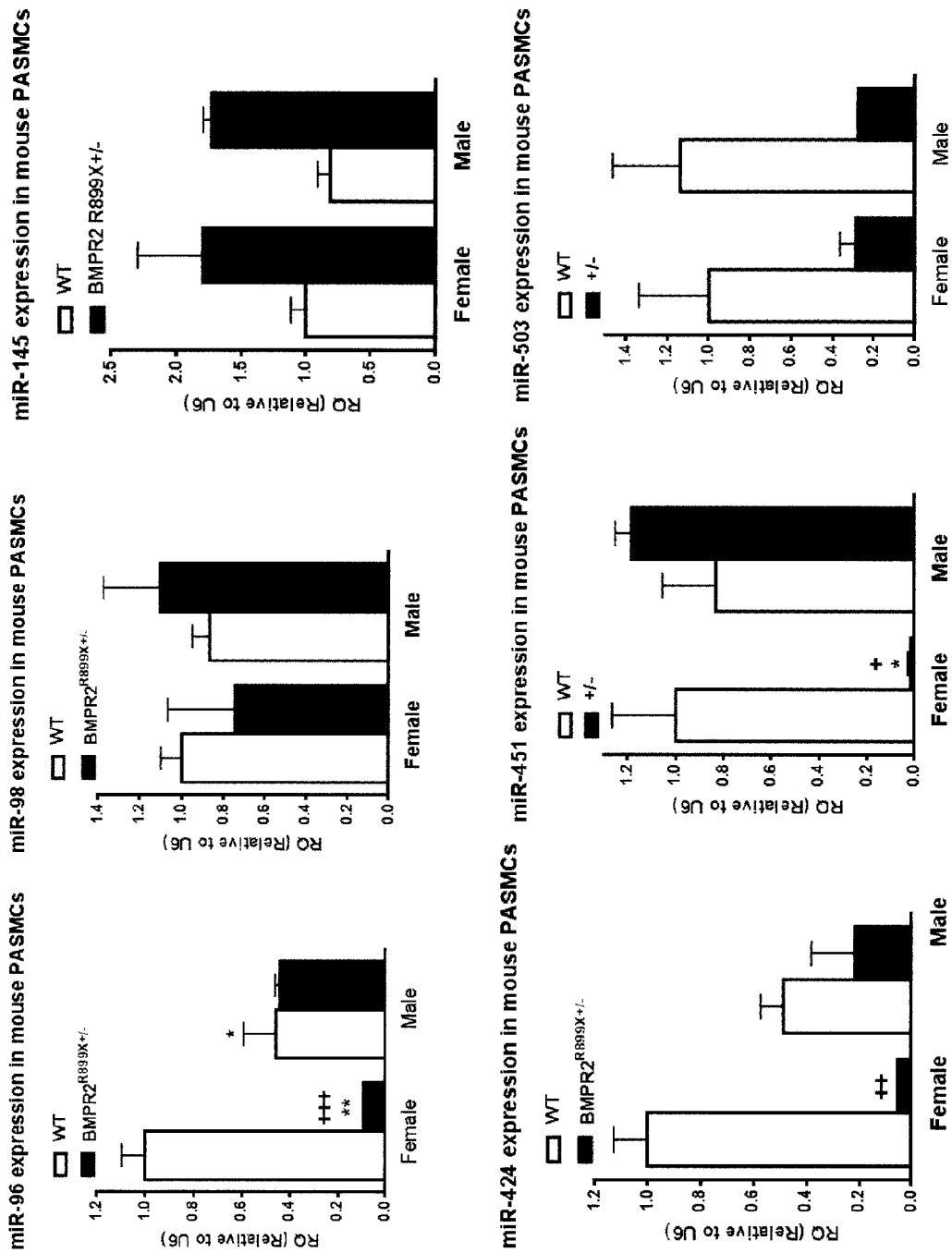
Fig. 1 (contd.)

SEQUENCE LISTING

<160> NUMBER OF SEQ ID NOS: 6

<210> SEQ ID NO 1

```
<211> LENGTH: 23
<212> TYPE: RNA
<213> ORGANISM: Homo sapiens

<400> SEQUENCE: 1
uuuggcacua gcacauuuuu gcu                                              23

<210> SEQ ID NO 2
<211> LENGTH: 22
<212> TYPE: RNA
<213> ORGANISM: Homo sapiens

<400> SEQUENCE: 2
aaucaugugc agugccaaua ug                                               22

<210> SEQ ID NO 3
<211> LENGTH: 78
<212> TYPE: RNA
<213> ORGANISM: Homo sapiens

<400> SEQUENCE: 3
uggccgauuu uggcacuagc acauuuuugc uugugucucu ccgcucugag caaucaugug      60
cagugccaau augggaaa                                                    78

<210> SEQ ID NO 4
<211> LENGTH: 106
<212> TYPE: RNA
<213> ORGANISM: Mus musculus

<400> SEQUENCE: 4
ccaguaccau cugcuuggcc gauuuuggca cuagcacauu uugcuugug ucucuccgcu       60 gugagcaauc augguagug ccaauauggg aaaagcgggc ugcugc                     106

<210> SEQ ID NO 5
<211> LENGTH: 2078
<212> TYPE: RNA
<213> ORGANISM: Homo sapiens

<400> SEQUENCE: 5
acacccugcc aucaccccuu ccccucccca cccaaggcug ggaagucugg ucucucuucc      60
uuaguagagu ucagaaaauu guaguaaggg aaacugaggc agaaggcuga ggagugacuu     120
ccugagauca ccaccucauc aagcuggauu guccucuggg agagauagacc agcuagaagg   180 gcagagcccu guagugggg uguguggag caggacaaag aguccucggg agcaggaagg      240
guggagcauu aagcagugu uaggggagag cggauggcuu uggccaaggu acccagaugg     300
agcucugagg uccacgggag guaguccug gggguaacau cgccaagagg ucugcauagu    360
uucugggcca gggcaccugc ucugacccuu ccaggauauu uucuagccac ccugccuucu    420
gggccaccgc ugaccuggag uaggcugaga cucuaguggc cacucugcgg aggcccagc    480 uugccugccc ugggugccag cucccccagag acccucccuc ccacccucuc ccuucuuccc    540
guccuucccc agggccugug acaccagagg cagggccucc acagcaacuu cucucuaggc    600
agcugcucug gcaaccacug augcaaccuu cccagcccu cccucgcucc ugagccuccg     660
cuuuccuccg cagucacucc agagccagcc aggagccacu cccuugcuag agugcauccg   720
ugccuccggc ucccuccaag ccaccuugu ggcugcagga cuucucuucu gcccuccuuu    780
ccuggccuuu uccugccuug auccuaggcc ggcagcagag augcccagcc uggggcgguuc   840 acagucuggc ccaaucuggu cugguuuggg augggagugg gggugagcag cagauucggu   900
```

| | | | | |
|---|---|---|---|---|
| uuguuccugg | ggcucuguuu | cugccacagg | gcaggcuggg | gggugagga uaauggagac | 960 |
| caaagugccu | aggagccugg | gcugcuggug | ucugggcuca | gaggcuacga gaggcaucuu | 1020 |
| ggauguccca | cuggucacug | cccugugggc | agguggguaa | gagaggaggc ucuggccagc | 1080 |
| ugcuugccuc | uccgagccag | aguuacucug | gcaaggagau | ggauggaucuu gacccacucc | 1140 |
| cuccccagcc | uggaggcgca | gucgggguga | ugggaggga | ugugggccuu cagguggaga | 1200 |
| uaggagacac | cuuggugugg | ucuucccuc | ugcaaggcca | gaaggucagc cccucucccg | 1260 |
| cacugucccu | gucuccuuga | aggucaucuu | gggcugaugg | ggcaugugga ucuugugaag | 1320 |
| aggugggaug | ggguggggg | uagagaccgu | agcagccgcu | gcugagggcc ugcugggggg | 1380 |
| cccccaaggg | aguggcagg | cuaggagcag | ggaacgggca | ucgugggccg cuggucucuc | 1440 |
| cgcaggucg | gcaggccgca | gagugugacu | ccguucugu | guauggcacu gguagaauuc | 1500 |
| acugugaaca | gucucaguca | gugaauuacc | gaagggccau | aaacagagca gagacagauc | 1560 |
| cacgagggcc | uccggagcac | cuuacccacu | ucugccuuga | gugucccuag acgucggaaa | 1620 |
| caggcugcuu | ccaagggugc | agggaugcaa | ggccccucgu | ccagugugue cccagagagc | 1680 |
| ccgcaccagu | gccaucugcu | uggccgauuu | uggcacuagc | acauuuugc uugucucu | 1740 |
| ccgcucugag | caaucaugug | cagugccaau | augggaaaag | caggacccgc agcugcgucc | 1800 |
| gccuccccug | cauccuugug | ucagggcccc | agccugcucc | uccucaaggc ccucucaccg | 1860 |
| ccucccagc | ccaucuggcu | cagcugcugu | gugagggccc | agcgcuggug ggcagccaga | 1920 |
| ucgccuuaca | cugccugggg | ccacgguaga | gcugggagcc | cagcaaucug agcugggcca | 1980 |
| gcagauggggg | ccgcccaggg | cagaggugg | ggagucugaa | accaucugua gggccauccu | 2040 |
| gaauggugcc | gugggnuugga | aaggcccagc | caggcucc | | 2078 |

<210> SEQ ID NO 6
<211> LENGTH: 2106
<212> TYPE: RNA
<213> ORGANISM: Mus musculus

<400> SEQUENCE: 6

| | | | | |
|---|---|---|---|---|
| gggcuauucu | cuuauggugc | uucauuccuu | ccugggugcu | ccagacugag uucucaggag | 60 |
| gacauuggua | cccugagugu | gucucaaucu | ucccaaggcc | cuuccccau ugcuacuccu | 120 |
| cuguuccauu | gaaaugggg | gggaaaaag | auuuuagaau | acuguuucca aaauauccug | 180 |
| caucuuuaga | gaaagcuguu | uccaagcaca | acucuaaaua | gcuucuccuu cccagcccuca | 240 |
| cauuccccag | guucauauua | aacuguaggu | uccucgugg | gccacaaagc uccauuucag | 300 |
| gggacuccuu | agugauucug | agaaacacuc | ugagccacau | agaacacacc aguaacuaua | 360 |
| gcuguccacc | cccgcuugac | uccucuaagu | ucagagauuu | auagggggg aaacugaggc | 420 |
| cacaggccag | ggagugucca | ucuuaccaag | augaauggc | cuuugggag gugagcuaga | 480 |
| gcuccagagu | cagcaaauag | ugaguuuucg | gucaaagccc | cacaaguaug uuaccaaguc | 540 |
| caggacugau | aacagguuua | cagugggguu | agccuggagu | aaaggcuuau aagguuucug | 600 |
| agcuggagaa | cucuaucuga | ccccuucccg | uauauuuccc | uuuccgucu accuuucccu | 660 |
| guggauucca | ggccggccua | agggauaggcu | gagccgugu | ugccuuuccc acagugucuc | 720 |
| cagcucucau | gcccugggca | ccagcuccag | agagacuuac | ccucccucuu uccuccaucc | 780 |
| ccagggcacc | ugguaccaga | ggcaagggcc | uccaucucugc | cuucucucgu ggcagccgcu | 840 |
| guagcaacca | cugacgcaac | cgccccagcc | ucccuuggc | ucuguagccu cuaccgudcu | 900 |

```
ccaaaguacu cucagaaccu uccagaggcu gcuuccgagg gcuccugcca gaaacaguuc    960
acccuggcuc cuuccgagcu gccuccuugu cugaaggagc ccccugcccu gauccuggcc   1020
cuggucaagc cacaaaggug cccaucgggg acacuuugca guccugccuu cugggccucu   1080
gcuuguguca cugggcaagc caggacugcu ggccucugug ccgagaggcc augagaagca   1140
cauuggaugu ucuugucacu gcccacuugg gaguagguga gguccagugc ccuagguuau   1200
gaggaucugg caacugcuug cugaccuugg caggaaggug gcuuguuugg gugaugguau   1260
ugggauguga ugggaaacuc ugcugcccuc ugcaagucca agaaaucaga cuuucuccuc   1320
acuuguccuu gucuucuuga aggacaauuu gggcuagugc acaacaacga gcuggugaag   1380
agcuggugag gaggguugcu aaacugcgga ugacagcagu ggggguggggg uggggggagu   1440 agguuguagg accuccagga gaaggcagcu gaccccucug cagggucugc aggcuggaga   1500
gugugacucc uguccugugu auggcacugg uagaauucac ugugaacagu cucagucagu   1560
gaauuaccga agggccauaa acagagcaga gacagauccg cgagcaccuu ggagcuccuc   1620
accccuuucu gccuagaccu cuguuuccag gggugccagg guacaaagac cuccucugcu   1680
ccuuccccag agggccuguu ccaguaccau cugcuuggcc gauuuuggca cuagcacauu   1740
uuugcuugug ucucuccgcu gugagcaauc auguguagug ccaauauggg aaaagcgggc   1800
ugcugcggcc acguucaccu cccccggcau cccaggggucu gugugucuca cuggcucccu   1860
ggcccaucug gcuuacugcu gggugaggag gguacagccc uacccugguug aacagccaga   1920 ucaccuuuca cugccugagg ccagagugga gucggagcug ggcaauccga gcugggccaa   1980
cagauggaga ugcuugcggu ggggguggggg gucgccaucu guagggccag cuucugugau   2040
gcccuguugg gcuccuccuc cuuaaggcga gccgucuuug gggucuagcc uucugcuaca   2100
ggauuc                                                              2106
```

MATERIALS AND METHODS FOR TREATMENT OF PULMONARY ARTERIAL HYPERTENSION

FIELD OF THE INVENTION

The invention relates to the use of microRNA 96 and precursors and mimics thereof for the inhibition of vascular cell proliferation and/or vascular remodelling, and for the treatment of associated medical conditions such as pulmonary arterial hypertension (PAH).

BACKGROUND TO THE INVENTION

Pulmonary arterial hypertension (PAH) is a devastating disease characterised by severe pulmonary arterial remodelling and occlusive pulmonary vascular lesions, leading to right ventricular failure. Recent epidemiological studies report the incidence of the disease is greater in females; depending on the disease classification the female to male ratio can be as great as 4:1[1].

PAH has a poor prognosis affecting 2-3/million annually; patients with PAH have a 1-, 3-, and 5-year survival rate of 68%, 48%, and 34%, respectively. Survival is not increased significantly on current therapies and there is an urgent need for novel therapeutic approaches.

Heritable PAH is associated with mutations in the gene for BMPR2 which signals through the smad1/ID pathway[2]. Serotonin also plays a key role in the development of PAH by facilitation PASMC proliferation and contraction. This can be via its synthesis by tryptophan hydroxylase 1 (TPH1) [3-5], by entering the cell via the serotonin transporter (SERT) and/or by activation of the 5HT1B receptor[3, 6-13].

We have demonstrated that, in three animal models of pulmonary hypertension (PH) where only the females develop PH (the SERT+ mouse[10], the mts1-over-expressing mouse[14] and the dexfenfluramine-treated mouse[15]), the development of PH can be serotonin-dependent and dependent on endogenous oestrogen and/or oestrogen metabolism[15-17]. This suggests that gender, oestrogen and serotonin are interacting risk factors in PH.

MicroRNAs (miRs) are small non-coding RNAs that have a substantial impact on cellular function through repression of translation (either through inhibition of translation or induction of mRNA degradation). MicroRNAs derive from primary RNA transcripts (pri-miRNA) synthesised by RNA pol II, which may be several thousand nucleotides in length. A single pri-miRNA transcript may give rise to more than one active miRNA.

In the nucleus, the Type III RNAse enzyme Drosha processes the pri-miRNA transcript into a precursor miRNA (pre-miRNA) consisting of a stem-loop or hairpin structure, normally around 70 to 100 nucleotides in length. The pre-miRNA is then transported to the cytoplasm, where it is processed further by the RNAse Dicer, removing the loop and yielding a mature double stranded miRNA molecule, having an active "guide" strand (typically 15 to 25 nucleotides in length) hybridised to a wholly or partially complementary "passenger" strand.

The mature double stranded miRNA is then incorporated into the RNA-induced silencing complex, where the guide strand hybridises to a binding site in the target mRNA.

The guide strand may not be completely complementary to the target binding site. However, a region of the guide strand designated the "seed" sequence is usually fully complementary to the corresponding sequence of the target binding site. The seed sequence is typically 2 to 8 nucleotides in length and located at or near (within 1 or two nucleotides of) the 5' end of the guide strand.

It is believed that single unpaired guide strands may also be capable of being incorporated into RISC. It is also believed that modifications to the passenger strand (e.g. to the sugars, the bases, or the backbone structure) which impede incorporation of the passenger strand into RISC may also increase efficiency of target inhibition by a double stranded miRNA.

Certain miRs have previously been shown to regulate genes that impact on PAH[18-20].

SUMMARY OF THE INVENTION

In its broadest form, the invention relates to the use of microRNA 96 (miR-96) and precursors, mimics and agonists thereof for the inhibition of vascular cell proliferation and/or vascular remodelling, and for the treatment of associated medical conditions such as PAH.

Without wishing to be bound by theory, it is believed that increasing miR-96 expression or activity in cells which express the 5-HT1B receptor may be particularly effective. Target cells include vascular cells and cells associated with the vasculature.

The invention provides a method for inhibiting vascular cell proliferation and/or vascular remodelling, comprising delivering to a target cell, or administering to a subject:
(a) miR-96, a mimic thereof, or a precursor of either; or
(b) a nucleic acid encoding miR-96, a mimic thereof, or a precursor of either.

The invention also provides a method for prophylaxis or treatment of pulmonary hypertension, comprising delivering to a target cell, or administering to a subject:
(a) miR-96, a mimic thereof, or a precursor of either; or
(b) a nucleic acid encoding miR-96, a mimic thereof, or a precursor of either.

The invention also provides miR-96, a mimic thereof, or a precursor of either, for use in a method of inhibiting vascular cell proliferation and/or vascular remodelling.

The invention also provides miR-96, a mimic thereof, or a precursor of either, for use in a method of prophylaxis or treatment of pulmonary hypertension, especially pulmonary arterial hypertension.

The invention also provides the use of miR-96, a mimic thereof, or a precursor of either, in the manufacture of a medicament for the inhibition of vascular cell proliferation and/or vascular remodelling.

The invention also provides the use of miR-96, a mimic thereof, or a precursor of either, in the manufacture of a medicament for the prophylaxis or treatment of pulmonary hypertension, especially pulmonary arterial hypertension.

The invention also provides a nucleic acid encoding miR-96, a mimic thereof, or a precursor of either, for use in a method of inhibiting vascular cell proliferation and/or vascular remodelling.

The invention also provides a nucleic acid encoding miR-96, a mimic thereof, or a precursor of either, for use in a method of prophylaxis or treatment of pulmonary hypertension, especially pulmonary arterial hypertension.

The invention also provides the use of a nucleic acid encoding miR-96, a mimic thereof, or a precursor of either, in the manufacture of a medicament for the inhibition of vascular cell proliferation and/or vascular remodelling.

The invention also provides the use of a nucleic acid encoding miR-96, a mimic thereof, or a precursor of either, in the manufacture of a medicament for the prophylaxis or treatment of pulmonary hypertension, especially pulmonary arterial hypertension.

In all aspects, the invention essentially involves increasing miR-96 activity in a target cell.

This may be achieved by direct delivery of miR-96 to the target cell, by delivery of a miR-96 mimic, or by delivery of a precursor molecule which is processed within the target cell to an active miR-96 or miR-96 mimic.

Alternatively, it may be achieved by delivering to the target cell a nucleic acid which encodes miR-96, a mimic thereof, or a precursor of either, such that active miR-96 or miR-96 mimic, or a precursor of either, is expressed within the target cell.

The target cell typically expresses the 5-HT1B receptor. The target cell may be a vascular cell, such as a vascular smooth muscle cell (VSMC) or a vascular endothelial cell. In particular, it may be a pulmonary artery smooth muscle cell (PASMC) or pulmonary artery endothelial cell. Alternatively, it may be a cell associated with the vasculature. A cell associated with the vasculature is a cell located within a blood vessel, or in the vessel wall, including the endothelium, smooth muscle or adventitia. The vasculature may be the pulmonary vasculature. The vasculature may be an artery, such as the pulmonary artery. Cells associated with the vasculature thus include adventitial fibroblasts and immune cells, e.g. lymphocytes (especially T lymphocytes), monocytes, macrophages and mast cells.

Methods involving delivery to a target cell may be performed in vitro, in vivo or ex vivo.

The miR-96, mimic or precursor may be delivered in association with (e.g. complexed with or encapsulated by) a suitable carrier molecule, such as a pharmaceutically acceptable lipid or polymer.

Nucleic acid encoding miR-96, a mimic or precursor, may be delivered as naked nucleic acid. Alternatively it may be delivered in association with (e.g. complexed with or encapsulated by) a suitable carrier molecule, such as a pharmaceutically acceptable lipid or polymer. In either case, the nucleic acid is typically DNA.

The carrier molecule may further comprise a targeting agent capable of binding to the surface of the target cell.

Alternatively, the nucleic acid encoding miR-96, a mimic or precursor, may be delivered via a viral vector.

Any suitable type of viral vector may be employed, including adenovirus, adeno-associated virus (AAV), retrovirus (especially lentivirus) and herpesvirus vectors. Adenovirus and lentivirus may be particularly preferred as they have the capacity to achieve expression of the gene(s) delivered in cells which are not actively dividing.

miR-96 and Precursors Thereof

The term "miR-96" is used in this specification to refer to an RNA oligonucleotide consisting of the sequence: UUUGGCACUAGCACAUUUUUGCU (SEQ ID NO: 1).

This is the sequence of mature miR-96 in most mammals, including human, gorilla, chimpanzee, orang-utan, macaque, marmoset, mouse, rat, rabbit, cow, pig, horse and dog.

Nucleotides 2 to 7 of the mature sequence are designated the "seed" region, which binds to the target mRNA, and have the sequence: UUGGCA.

The active miR-96 oligonucleotide (or "guide strand") may be single stranded, or it may be hybridised with a second RNA oligonucleotide, referred to as a "passenger strand". The guide strand and passenger strand run antiparallel to one another in the hybridised complex, which may be referred to as "double stranded miR-96". The guide strand, when present in isolation, may be referred to as "single stranded miR-96".

The passenger strand and the guide strand may contain a number of mis-matches with the result that not all nucleotides in one or both strands hybridise to complementary nucleotides in the other strand. Thus the double stranded miR-96 may contain one or more bulges (a bulge is an unpaired nucleotide, or plurality of consecutive unpaired nucleotides, in one strand only) or internal loops (opposed unpaired nucleotides in both strands). One or more nucleotides at the termini may also be unpaired.

The passenger strand may be 100% complementary to the seed sequence of the guide strand.

One or both strands of double stranded miR-96 may comprise a 3' overhang, e.g. of 1, 2 or 3 nucleotides. That is to say, nucleotides at the 3' terminus of the strand extend beyond the most 5' nucleotide of the complementary strand (including unpaired terminal nucleotides) and thus have no corresponding nucleotides in the complementary strand. For example, both strands may comprise a 3' overhang of 1, 2 or 3 nucleotides. Alternatively the complex may be blunt-ended at one or both ends. In some embodiments, the passenger strand is the same length as the guide strand, or differs in length, e.g. by up to five nucleotides or even more, depending on the degree of mismatch between the two strands and the lengths of any 3' overhang.

The mature native miR-96 passenger strand has the sequence:
5'-AAUCAUGUGCAGUGCCAAUAUG-3' (SEQ ID NO: 2) and is believed to pair with the guide strand as follows:

```
Guide:       5'    UUUGGCACUAGCACAUUUUUGCU 3'    (SEQ ID NO: 1)
                   |||||||||  |||||   ||
Passenger:   3' GUAUAACCGUGA-CGUGUACUAA    5'    (SEQ ID NO: 2)
```

Thus the passenger strand has a 3' unpaired nucleotide and a 3 nucleotide 3' overhang. The guide strand has a 3 nucleotide 3' overhang. The hybridised complex has three regions of complementarity (one of which includes all of the seed sequence) separated by one bulge in the guide strand and an internal loop.

Precursors of miR-96 include pre-mir-96 and pri-mir-96, as well as fragments and variants thereof which can be processed to mature miR-96 (whether single or double stranded).

The term "pre-mir-96" is used to refer to an RNA oligonucleotide consisting of any full-length mammalian pre-mir-96 sequence, or a fragment or variant thereof which comprises a mature miR-96 guide sequence connected by a loop sequence to a corresponding passenger sequence which is fully or partially complementary to the guide sequence, and wherein the oligonucleotide is capable of forming a stem-loop structure (or "hairpin") in which the guide sequence and passenger sequence hybridise to one another.

A pre-mir-96 is capable of acting as a substrate for the double-stranded RNA-specific ribonuclease (RNAse III-type enzyme) Dicer, whereby it is processed to a mature double stranded miR-96.

Full-length mammalian pre-mir-96 sequences include the human sequence (hsa-pre-mir-96):

(SEQ ID NO: 3)
UGGCCGAU<u>UUUGGCACUAGCACAUUUUUGC</u>UUGUGUCUCUCCGCUCUGAG
CAAUCAUGUGCAGUGCCAAUAUGGGAAA;

and the murine sequence (mmu-pre-mir-96):

(SEQ ID NO: 4)
CCAGUACCAUCUGCUUGGCCGAU<u>UUUGGCACUAGCACAUUUUUGC</u>UUGUG
UCUCUCCGCUGUGAGCAAUCAUGUGUAGUGCCAAUAUGGGAAAAGCGGGC
UGCUGC.

In both cases, the mature sequence (of the guide strand) is underlined.

The pre-mir-96 may possess one or more modifications outside the mature sequence, compared to the sequences shown.

The sequence upstream (5') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence. For example, the sequence upstream may differ by 1, 2, 3 or 4 nucleotides from the 5' human sequence when optimally aligned therewith, or may differ by 1, 2, 3, 4, 5, 6, 7, 8, 9, 10 or 11 nucleotides from the 5' murine sequence when optimally aligned therewith.

The sequence downstream (3') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence. For example, the sequence downstream may differ by up to 5, up to 10, up to 15 or up to 20 nucleotides from the 3' human sequence when optimally aligned therewith, or may differ by up to 5, up to 10, up to 15, up to 20, up to 25 or up to 30 nucleotides from the 3' murine sequence when optimally aligned therewith.

The term "pri-mir-96" is used to refer to an RNA oligonucleotide consisting of any full-length mammalian pri-mir-96 sequence, or a fragment or variant thereof which comprises a pre-mir-96 sequence and is capable of being processed to a pre-mir-96 sequence by the double-stranded RNA-specific ribonuclease (RNAse III-type enzyme) Drosha.

Full-length mammalian pri-mir-96 sequences include the human sequence (hsa-pri-mir-96) (SEQ ID NO: 5):

ACACCCUGCCAUCACCCCUUCCCUCCCCACCCAAGGCUGGGAAGUCUGG

UCUCUCUUCCUUAGUAGAGUUCAGAAAAUUGUAGUAAGGGAAACUGAGGC

AGAAGGCUGAGGAGUGACUUCCUGAGAUCACCACCUCAUCAAGCUGGAUU

GUCCUCUGGGGAGAUAGACCAGCUAGAAGGGCAGAGCCCUGUAGUGGGGG

UGUGUGGGAGCAGGACAAAGAGUCCUCGGGAGCAGGAAGGGUGGAGCAUU

AAGCAGUGUCUAGGGGAGAGCGGAUGGCUUUGGCCAAGGUACCCAGAUGG

AGCUCUGAGGUCCACGGGAGGUAGUUCCUGGGGGUAACAUCGCCAAGAGG

UCUGCAUAGUUUCUGGGCCAGGGCACCUGCUCUGACCCUUCCAGGAUAUU

UUCUAGCCACCCUGCCUUCUGGGCCACCGCUGACCUGGAGUAGGCUGAGA

CUCUAGUGGCCACUCUGCGGAGGCCCCAGCUUGCCUGCCCUGGGUGCCAG

CUCCCCAGAGACCCUCCCUCCCACCCUCUCCCUUCUUCCCGUCCUUCCCC

AGGGCCUGUGACACCAGAGGCAGGGCCUCCACAGCAACUUCUCUCUAGGC

AGCUGCUCUGGCAACCACUGAUGCAACCUUCCCAGCCCCUCCCUCGCUCC

UGAGCCUCCGCUUUCCUCCGCAGUCACUCCAGAGCCAGCCAGGAGCCACU

CCCUUGCUAGAGUGCAUCCGUGCCUCCGGCUCCCUCCAAGCCACCUGGGU

GGCUGCAGGACUUCUCUUCUGCCCUCCUUUCCUGGCCUUUUCCUGCCUUG

AUCCUAGGCCGGCAGCAGAGAUGCCCAGCCUGGGCGGUUCACAGUCUGGC

CCAAUCUGGUCUGGUUUGGGAUGGGAGUGGGGGUGAGCAGCAGAUUCGGU

UUGUUCCUGGGGCUCUGUUUCUGCCACAGGGCAGGCUGGGGGGUGGAGGA

UAAUGGAGACCAAAGUGCCUAGGAGCCUGGGCUGCUGGUGUCUGGGCUCA

GAGGCUACGAGAGGCAUCUUGGAUGUCCCACUGGUCACUGCCCCUGUGGC

AGGUUGGGUAGAGAGGAGGCUCUGGCCAGCUGCUUGCCUCUCCGAGCCAG

AGUUACUCUGGCAAGGAGAUGGAUGGUCCUGACCCACUCCCUCCCCAGCC

UGGAGGCGCAGUCUGGGUGAUGUGGAGGGAUGUGGGCCUUCAGGUGGAGA

UAGGAGACACCUUGGUGUGGUCUUCUCCUCUGCAAGGCCAGAAGGUCAGC

UCCUCUCCCGCACUGUCCCUGUCUCCUUGAAGGUCAUCUUGGGCUGAUGG

GGCAUGUGGAUCUUGUGAAGAGGUGGGAUGGGGUGGGGGGUAGAGACCGU

AGCAGCCGCUGCUGAGGGCCUGCUGGGGGGCCCCCAAGGGAGUGGGCAGG

CUAGGAGCAGGGAACGGGCAUCGUGGGCCGCUGGUCUCUCCGCAGGGUCG

GCAGGCCGCAGAGUGUGACUCCUGUUCUGUGUAUGGCACUGGUAGAAUUC

ACUGUGAACAGUCUCAGUCAGUGAAUUACCGAAGGGCCAUAAACAGAGCA

GAGACAGAUCCACGAGGGCCUCCGGAGCACCUUACCCACUUCUGCCUUGA

GUGCUCCUAGACGUCGGAAACAGGCUGCUUCCAAGGGUGCAGGGAUGCAA

GGCCCCUCGUCCAGUGUGUCCCCAGAGAGCCCGCACCAGUGCCAUCUGCU

UGGCCGAU<u>UUUGGCACUAGCACAUUUUUGC</u>UUGUGUCUCUCCGCUCUGAG

CAAUCAUGUGCAGUGCCAAUAUGGGAAAAGCAGGACCCGCAGCUGCGUCC

GCCUCCCCUGCAUCCUUGUGUCAGGGCCCCAGCCUGCUCCUCCUCAAGGC

CUCCUCACCGCCUCCCCAGCCCAUCUGGCUCAGCUGCUGUGUGAGGGCCC

AGCGCUGGUGGGCAGCCAGAUCGCCUUACACUGCCUGGGGCCACGGUAGA

GCUGGGAGCCCAGCAAUCUGAGCUGGGCCAGCAGAUGGGGCCGCCCAGGG

CAGAGGUGGGGAGUCUGAAACCAUCUGUAGGGCCAUCCUGAAUGGUGCC

GUGGGUUGGAAAGGCCCAGCCAGGCUCC and the murine sequence (mmu-pri-mir-96):

(SEQ ID NO: 6)
GGGCUAUUCUCUUAUGGUGCUUCAUUCCUUCCUGGGUGCUCCAGACUGAG

UUCUCAGGAGGACAUUGGUACCCUGAGUGUGUCUCAAUCUUCCCAAGGCC

-continued
CUUCCCCCAUUGCUACUCCUCUGUUCCAUUGAAAUGGGGGGGGAAAAAG

AUUUUAGAAUACUGUUUCCAAAAUAUCCUGCAUCUUUAGAGAAAGCUGUU

UCCAAGCACAACUCUAAAUAGCUUCUCCUUCCCAGCCUCACAUUCCCAG

GUUCAUAUUAAACUGUAGGUUUCCUCGUGGGCCACAAAGCUCCAUUUCAG

GGGACUCCUUAGUGAUUCUGAGAAACACUCUGAGCCACAUAGAACACACC

AGUAACUAUAGCUGUCCACCCCCGCUUGACUCCUCUAAGUUCAGAGAUUU

AUAGUGGGGGAAACUGAGGCCACAGGCCAGGGAGUGUCCAUCUUACCAAG

AUGAAAUGGCCUUUUGGGAGGUGAGCUAGAGCUCCAGAGUCAGCAAAUAG

UGAGUUUUCGGUCAAAGCCCCACAAGUAUGUUACCAAGUCCAGGACUGAU

AACAGGUUUACAGUGGGGUUAGCCUGGAGUAAAGGCUUAUAAGGUUUCUG

AGCUGGAGAACUCUAUCUGACCCCUUCCCGUAUAUUUCCUUUUCCGUCU

ACCUUUCCCUGUGGAUUCCAGGCCGGCCUAAGGGUAGGCUGAGCCUGUGU

UGCCUCUUCCACAGUGUCUCCAGCUCUCAUGCCCUGGGCACCAGCUCCAG

AGAGACUUACCCUCCCUCUUUCCUCCAUCCCCAGGGCACCUGGUACCAGA

GGCAAGGGCCUCCAUCCUGCCUUCUCUCGUGGCAGCCGCUGUAGCAACCA

CUGACGCAACCGCCCCAGCCCUCCCUUGGCUCUGUAGCCUCUACCGUCCU

CCAAAGUACUCUCAGAACCUUCCAGAGGCUGCUUCCGAGGGCUCCUGCCA

GAAACAGUUCACCCUGGCUCCUUCCGAGCUGCCUCCUUGUCUGAAGGAGC

CCCCUGCCUGAUCCUGGCCCUGGUCAAGCCACAAAGGUGCCCAUCGGGG

ACACUUUGCAGUCCUGCCUUCUGGGCCUCUGCUUGUGUCACUGGGCAAGC

CAGGACUGCUGGCCUCUGUGCCGAGAGGCCAUGAGAAGCACAUUGGAUGU

UCUUGUCACUGCCCACUUGGGAGUAGGUGAGGUCCAGUGCCCUAGGUUAU

GAGGAUCUGGCAACUGCUUGCUGACCUUGGCAGGAAGGUGGCUUGUUUGG

GUGAUGGUAUUGGGAUGUGAUGGGAAACUCUGCUGCCCUCUGCAAGUCCA

AGAAAUCAGACUUUCUCCUCACUUGUCCUUGUCUUCUUGAAGGACAAUUU

GGGCUAGUGCACAACAACGAGCUGGUGAAGAGCUGGUGAGGAGGGUUGCU

AAACUGCGGAUGACAGCAGUGGGGUGGGUGGGGGAGUAGGUUGUAGG

ACCUCCAGGAGAAGGCAGCUGACCCCUCUGCAGGGUCUGCAGGCUGGAGA

GUGUGACUCCUGUCCUGUGUAUGGCACUGGUAGAAUUCACUGUGAACAGU

CUCAGUCAGUGAAUUACCGAAGGGCCAUAAACAGAGCAGAGACAGAUCCG

CGAGCACCUUGGAGCUCCUCACCCCUUUCUGCCUAGACCUCUGUUUCCAG

GGGUGCCAGGGUACAAAGACCUCCUCUGCUCCUUCCCCAGAGGGCCUGUU

CCAGUACCAUCUGCUUGGCCGAUUUUGGCACUAGCACAUUUUUGCUUGUG

UCUCUCCGCUGUGAGCAAUCAUGUGUAGUGCCAAUAUGGGAAAAGCGGGC

UGCUGCGGCCACGUUCACCUCCCCCGGCAUCCCAGGGUCUGUGUGUCUCA

CUGGCUCCCUGGCCCAUCUGGCUUACUGCUGGGUGAGGAGGGUACAGCCC

UACCCUGGUGAACAGCCAGAUCACCUUUCACUGCCUGAGGCCAGAGUGGA

GUCGGAGCUGGGCAAUCCGAGCUGGGCCAACAGAUGGAGAUGCUUGCGGU

GGGGGUGGGGGUCGCCAUCUGUAGGGCCAGCUUCUGUGAUGCCCUGUUGG

GCUCCUCCUCCUUAAGGCGAGCCGUCUUUGGGGUCUAGCCUUCUGCUACA

GGAUUC.

Again, the mature sequences are underlined.

The pri-mir-96 may possess one or more modifications outside the mature sequence or outside the native pre-mir-96 sequence, compared to the sequences shown.

For example, the sequence upstream (5') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

The sequence upstream (5') of the pre-mir-96 sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

The sequence downstream (3') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

The sequence downstream (3') of the native pre-mir-96 sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

The miR-96 precursor may be any suitable length, as long as it can be processed to mature miR-96 (whether single or double stranded). Thus the precursor is at least 23 nucleotides in length, and may be at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 200, at least 250, at least 300, at least 350, at least 400, at least 450, at least 500, at least 1000, at least 1500 or at least 2000 nucleotides in length.

Alternatively, the precursor may be a maximum of 25, 30, 35, 40, 45, 50, 55, 60, 65, 70, 75, 80, 85, 90, 95, 100, 110, 120, 130, 140, 150, 200, 250, 300, 350, 400, 450, 500, 1000, 1500, 2000 or 2500 nucleotides in length.

It should be noted that the term "oligonucleotide" is not intended to imply any particular length, and is simply used to refer to any single continuous chain of linked nucleotides.

miR-96 Mimics and Precursors Thereof

A miR-96 mimic is an oligonucleotide which has one or more modifications in structure or sequence compared to naturally-occurring miR-96 but retains the ability to hybridise to a miR-96 binding site in mRNA regulated by miR-96, and to inhibit expression of the 5-HT1B receptor. mRNAs regulated by miR-96 include those (such as 5-HT1B mRNA) whose translation is inhibited or whose degradation is accelerated by binding of miR-96.

An example of a miR-96 binding site is the sequence TGTGCTAGTGCCAAA, found in Htr1b mRNA (i.e. the gene encoding the 5HT1B receptor).

A miR-96 mimic oligonucleotide is typically 15-25 nucleotides in length, e.g. 18 to 25, 20 to 25, e.g. 20 to 23, e.g. 20, 21, 22 or 23 nucleotides in length.

The miR-96 mimic may differ in base sequence, nucleotide structure, and/or backbone linkage as compared to miR-96.

The miR-96 mimic typically comprises a seed sequence which is identical to the native seed sequence:
UUGGCA.

The miR-96 mimic may comprise or consist of an oligonucleotide having the mature native sequence:

UUUGGCACUAGCACAUUUUUGCU                (SEQ ID NO: 1)

(wherein the seed sequence is underlined).

The miR-96 mimic may differ from the mature native sequence outside the seed sequence. For example, it may differ from the mature native sequence at 1, 2, 3, 4, 5, 6, 7, 8, 9 or 10 positions, all of which must lie outside the seed sequence.

The miR-96 mimic may be hybridised to a second oligonucleotide. As with the native miR-96, the active oligonucleotide may be referred to as the "guide strand" and the associated oligonucleotide as the "passenger strand". The hybridised complex may be referred to as a double stranded miR-96 mimic.

The sequence of the mimic passenger strand may be identical to the sequence of the native passenger strand or may differ from the native passenger strand at one or more positions. For example, the sequence of the mimic passenger strand may differ from that of the native passenger strand at no more than 10 positions, no more than 9 positions, no more than 8 positions, no more than 7 positions, no more than 6 positions, no more than 5 positions, no more than 4 positions, no more than 3 positions, no more than 2 positions or no more than 1 position. Preferably the passenger strand is 100% complementary to the seed sequence of the guide strand and any differences in sequence between the mimic sequence and the native sequence occur outside the region complementary to the seed sequence.

One or both strands of a double stranded miR-96 mimic may comprise a 3' overhang, e.g. of 1, 2 or 3 nucleotides. For example, both strands may comprise a 3' overhang of 3 nucleotides. Alternatively the complex may be blunt-ended at one or both ends. The passenger strand and the guide strand may contain one or more mis-matches. In some embodiments, the passenger strand is the same length as the guide strand, or differs in length by up to 5 nucleotides.

A precursor of a miR-96 mimic is any molecule which can be processed within the target cell to a miR-96 mimic, typically by action of the enzyme Dicer or by sequential action of the enzymes Drosha and Dicer.

Thus a precursor may have additional oligonucleotide sequence upstream (5') and/or downstream (3') of the mimic sequence.

The precursor may comprise the miR-96 mimic guide sequence connected by a loop sequence to a corresponding passenger sequence which is fully or partially complementary to the guide sequence, and wherein the oligonucleotide is capable of forming a stem-loop structure (or "hairpin") in which the guide sequence and passenger sequence hybridise to one another. Such an oligonucleotide may be regarded as a pre-mir-96 mimic and is capable of acting as a substrate for the double-stranded RNA-specific ribonuclease (RNAse III-type enzyme) Dicer, whereby it is processed to a double stranded miR-96 mimic, comprising separate guide and passenger strands.

The sequence upstream (5') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

The sequence downstream (3') of the mature sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

Alternatively, the precursor may be a pri-mir-96 mimic (i.e. it has additional oligonucleotide sequence upstream (5') and/or downstream (3') of the pre-mir-96 mimic sequence) and be capable of being processed to a pre-mir-96 mimic sequence by the double-stranded RNA-specific ribonuclease (RNAse III-type enzyme) Drosha.

For example, the sequence upstream (5') of the mature miR-96 mimic sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding native human or murine sequence.

The sequence upstream (5') of the pre-mir-96 mimic sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

The sequence downstream (3') of the mature miR-96 mimic sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

The sequence downstream (3') of the pre-mir-96 mimic sequence may have, for example, at least 50% identity, at least 55% identity, at least 60% identity, at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity with the corresponding human or murine sequence.

The miR-96 mimic precursor may be any suitable length, as long as it can be processed to mature miR-96 mimic (whether single or double stranded). Thus the precursor is at least 23 nucleotides in length, and may be at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 200, at least 250, at least 300, at least 350, at least 400, at least 450, at least 500, at least 1000, at least 1500 or at least 2000 nucleotides in length.

Alternatively, the precursor may be a maximum of 25, 30, 35, 40, 45, 50, 55, 60, 65, 70, 75, 80, 85, 90, 95, 100, 110, 120, 130, 140, 150, 200, 250, 300, 350, 400, 450, 500, 1000, 1500, 2000 or 2500 nucleotides in length.

Structural Modifications

In addition to, or as an alternative to the sequence modifications discussed above, a miR-96 mimic or precursor thereof may comprise one or more structural modifications compared to an RNA oligonucleotide.

The miR-96 mimic or precursor may comprise one or more nucleotides comprising a modified sugar residue, i.e. a sugar residue other than a ribose residue.

Modified sugar residues include carbocyclic or acyclic sugars, sugars having substituent groups at one or more of their 2', 3' or 4' positions and sugars having substituents in place of one or more hydrogen atoms of the sugar.

Suitable modified sugars may possess a sugar substituent group selected from: OH; F; O-, S-, or N-alkyl; O-, S-, or N-alkenyl; O-, S- or N-alkynyl; or O-alkyl-O-alkyl. The alkyl, alkenyl and alkynyl may be substituted or unsubstituted C1 to C10 alkyl or $C_2$ to C10 alkenyl and alkynyl. In some embodiments, these groups may be chosen from: $O(CH_2)_xOCH_3$, $O((CH_2)_xO)_yCH_3$, $O(CH_2)_xNH_2$, $O(CH_2)_xCH_3$, $O(CH_2)_xONH_2$, and $O(CH_2)_xON((CH_2)_xCH_3)_2$, where x and y are from 1 to 10.

Sugar substituent groups may include $C_1$ to $C_{10}$ lower alkyl, substituted lower alkyl, alkenyl, alkenyl, alkaryl, aralkyl, O-alkaryl or O-aralkyl, SH, $SCH_3$, CI, Br, CN, OCN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino and substituted silyl.

Other substituent groups include 2'-methoxyethoxy and 2'-dimethylaminoethoxyethoxy, allyl (—$CH_2$—CH=$CH_2$), —O-allyl (—O—$CH_2$—CH=$CH_2$), methoxy-O—$CH_3$), aminopropoxy (—$OCH_2CH_2CH_2NH_2$) and fluoro (F).

Sugar substituent groups on the 2' position (2'-) may be in the arabino (up) position or ribo (down) position. One 2'-arabino modification is 2'-F. Other similar modifications may also be made at other positions on the oligomeric compound, particularly the 3' position of the sugar on the 3' terminal nucleoside or in 2'-5' linked oligonucleotides and the 5' position of 5' terminal nucleotide.

Examples of modified sugar residues include 2'-O-methyl ribose, 2'-O-methoxyethyl ribose, 2'-fluoro-ribose and 4-thio-ribose.

Bicyclic sugars may also be used and typically comprise a furanosyl ring with a 2',4' bridge (e.g. a methylene bridge) which constrains the ring to the C3' endo configuration. A nucleotide containing a bicyclic sugar is often referred to as a locked nucleic acid ("LNA") residue.

The miR-96 mimic or precursor may independently contain one or more of any or all of these types of modified sugar residues.

Additionally or alternatively, the miR-96 mimic or precursor may comprise one or more backbone modifications, e.g. a modified internucleoside linkage.

Thus, one or more adjacent nucleotides may be joined via an alternative linkage moiety instead of a phosphate moiety.

It may be particularly desirable for a modified internucleoside linkage to be present at one or both ends of the miR-96 mimic, i.e. between the 5' terminal nucleotide and the adjacent nucleotide, and/or between the 3' terminal nucleotide and the adjacent nucleotide.

Moieties suitable for use as internucleoside linkages include phosphorothioate, morpholino and phosphonocarboxylate moieties, as well as siloxane, sulphide, sulphoxide, sulphone, acetyl, formacetyl, thioformacetyl, methylene formacetyl, thioformacetyl, alkenyl, sulphamate, methyleneimino, methylenehydrazino, sulphonate and sulphonamide moieties.

In a phosphorothioate moiety, a non-bridging oxygen atom is replaced by a sulphur atom. Phosphorothioate groups may promote serum protein binding and may thus improve in vivo distribution and bioavailability of the mimic. This may be desirable if the mimic is to be administered systemically to the recipient.

Additionally or alternatively, the miR-96 mimic or precursor may comprise one or more modified bases as alternatives to the naturally occurring adenine, cytosine, guanine and uracil. Such modified bases include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (including 5-bromo, 5-trifluoromethyl and other 5-substituted uracils and cytosines), 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Delivery of miR-96, Mimics and Precursors

Compositions may be provided in which miR-96, mimics and precursors are associated with (e.g. complexed with or encapsulated by, or covalently attached to) a suitable carrier.

Suitable carriers include pharmaceutically acceptable lipids and polymers, and combinations thereof. For example, the composition may have the form of liposomes, lipid vesicles, lipid complexes or polymer complexes.

For example, lipid vesicles and liposomes are lipid bilayer particles having an aqueous core containing the oligonucleotide cargo.

Lipid complexes (or "lipoplexes") and polymer complexes ("polyplexes") typically contain positively charged lipids or polymers which interact with the negatively charged oligonucleotides to form complexes.

The cationic polymers or lipids may also interact with negatively charged molecules at the surface of the target cells. By suitable choice of lipids and head groups, the complexes can be tailored to facilitate fusion with the plasma membrane of the target cell or with a selected internal membrane (such as the endosomal membrane or nuclear membrane) to facilitate delivery of the oligonucleotide cargo to the appropriate sub-cellular compartment. Gene delivery by lipoplexes and polyplexes is reviewed, for example, by Tros de Ilarduya et al. in Eur. J. Pharm. Sci. 40 (2010) 159-170.

Neutral lipid emulsions may also be used to form particulate complexes with miRNAs having diameters of the order of nanometers.

Appropriate lipids may be selected by the skilled person depending on the application, cargo and the target cell. Single lipids may be used, or, more commonly, combinations of lipids.

Suitable lipids are described, for example, in WO2011/088309 and references cited therein, and include:

neutral lipids and phospholipids, such as sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, dilinoleoylphosphatidylcholine, phosphatidylcholine (PC), 1,2-Dioleoyl-sn-glycero-3-phosphocholine (DOPC), lecithin, phosphatidylethanolamine (PE), lysolecithin, lysophosphatidylethanolamine, sphinogomyelin (SM), cardiolipin, phosphosphatidic acid, 1,2-Distearoyl-sn-glycero-3-phosphocholine (DSPC), 1,2-Dipalmitoyl-sn-glycero-3-phosphoethanolamine (DPPE), 1-Palmitoyl-2-oleoyl-sn-glycero-3-phosphocholine (POPC), 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Dimyristoyl-sn-glycero-3-phosphoethanolamine (DMPE), 1,2-Dioleoyl-sn-glycero-3-phosphoethanolamine (DOPE), dipalmitoloeoyl-PE, diphytanoyl-PE, DSPE, dielaidoyl-PE, dilinoleoyl-SM, and dilinoleoyl-PE;

sterols, e.g. cholesterol polymer-modified lipids, e.g. polyethylene glycol (PEG) modified lipids, including PEG-modified phosphatidylethanolamine and phosphatidic acid, PEG-ceramide conjugates, PEG-modified dialkylamines and PEG-modified 1,2-diacyloxypropan-3-amines. Particularly suitable are PEG-modified diacylglycerols and dialkylglycerols, e.g. PEG-didimyristoyl glycerol (PEG-DMG) PEG-distyryl glycerol (PEG-DSG) and PEG-carbamoyl-1,2-dimyristyloxypropylamine (PEG-CDMA);

cationic lipids, such as N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammoniumbromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), N-(1,2-dimyristyloxyprop-3-yl)-N,N-dimethyl-N-hydroxyethyl ammonium bromide ("DMRIE"), 1,2-dilinoleyloxy-3-dimethylaminopropane (DLinDMA) 1,2-Dilinoleoyl-3-dimethylaminopropane (DLinDAP), 1-Linoleoyl-2-linoeyloxy-3-dimethylaminopropane (DLin-2-DMAP), 1,2-Dilinoleylcarbamoyloxy-3-dimethylaminopropane (DLin-C-DAP), 1,2-Dilinoleylthio-3-dimethylaminopropane (DLin-S-DMA), and 2,2-Dilinoleyl-4-10 dimethylaminomethyl-[1,3]-dioxolane (DLin-K-DMA). Commercial preparations of cationic lipids include Lipofectin™ (comprising DOTMA and DOPE, available from Gibco/BRL), and Lipofectamine™ (comprising DOSPA and DOPE, available from Gibco/BRL).

anionic lipids including phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine and lysylphosphatidylglycerol.

WO/0071096 describes different formulations, such as a DOTAP:cholesterol or cholesterol derivative formulation that can effectively be used for oligonucleotide delivery.

A commercially available composition capable of achieving good delivery of miRNA to the lungs is the neutral lipid emulsion MaxSuppressor in vivo RNALancerII (BIOO Scientific, Austin, Tex.) which consists of 1,2-dioleoyl-sn-glycero-3-phosphocholine, squalene oil, polysorbate 20 and an antioxidant. In complex with synthetic miRNAs, it forms nanoparticles in the nanometer diameter range.

Suitable polymers include histones and protamines (and other DNA-binding proteins), poly(ethyleneimine) (PEI), cationic dendrimers such as polyamidoamine (PAMAM) dendrimers, 2-dimethyl(aminoethyl) methacrylate (pD-MAEM), poly(L-lysine) (PLL), carbohydrate-based polymers such as chitosan, etc. See Tros de Ilarduya et al. in Eur. J. Pharm. Sci. 40 (2010) 159-17 for a review. Proteins and peptides such as atellocolalgen can be used. Atellocollagen is a water soluble form of collagen produced by protease treatment, in particular pepsin-treated type I collagen from calf dermis.

Cyclodextrins may also be of use for delivery.

Additionally or alternatively, a miR-96 mimic or precursor may comprise a membrane transport moiety, to facilitate transit across the target cell's plasma membrane. This moiety may be a suitable lipid or other fatty moiety, including but not limited to cholesterol and stearoyl moieties. Other membrane transport moieties include cell penetrating peptides ("CPPs", such as TAT and MPG from HIV-1, penetratin, polyarginine) and fusogenic peptides (e.g. endodomain derivatives of HIV-1 envelope (HGP) or influenza fusogenic peptide (diINF-7)). The membrane transit moiety may be conjugated to a carrier molecule which is non-covalently associated with the miR-96 mimic or precursor itself. Alternatively a membrane transit moiety may be conjugated to the miR-96 mimic or precursor itself. The moiety may be conjugated to either the guide strand or the passenger strand, although the passenger strand is preferred, so as not to impair guide strand function. Conjugation at either the 5' or the 3' terminus may be preferred, although conjugation to an internal residue is also possible.

For the avoidance of doubt, a miR-96 molecule (i.e. not otherwise possessing any structural or sequence differences from the native molecule) could be considered a miR-96 mimic or precursor when linked to a membrane transit moiety.

Target Cells

The target cells in which miR-96 activity is to be increased are typically vascular cells, or cells associated with the vasculature.

A cell associated with the vasculature is a cell located within a blood vessel, or in the vessel wall, including the endothelium, smooth muscle or adventitia.

Typically the vasculature is the pulmonary vasculature, especially the pulmonary artery.

Thus vascular smooth muscle cells and vascular endothelial cells are target cells, especially pulmonary vascular smooth muscle cells and pulmonary vascular endothelial cells, particularly pulmonary artery smooth muscle cells and pulmonary artery endothelial cells.

The target cells typically express the 5-HT1B receptor, constitutively, although expression may be modulated, e.g. increased, under conditions of hypertension, or under conditions conducive to the development of hypertension.

5HT1B receptors are expressed on many cells that play a role in the immune response and inflammation, including T-lymphocytes and mononuclear cells such as monocytes and macrophages (22-24). A dysfunctional immune system, involving T lymphocytes and inflammatory cells, contributes to PAH pathogenesis (25, 26). In addition, serotonin stimulates DNA synthesis in fibroblasts through 5-HT1B receptors and this is associated with proliferation of fibroblasts in models of PAH (27, 28).

Thus, adventitial fibroblasts and immune cells which express the 5-HT1B receptor also represent target cells, including T lymphocytes, monocytes, macrophages and mast cells.

Targeting Agents

Carrier molecules may also carry targeting agents capable of binding to the surface of the target cell. For example, the targeting agent may be a specific binding partner, capable of binding specifically to a molecule expressed on the surface of a target cell, e.g. a vascular smooth muscle cell (e.g. pulmonary artery smooth muscle cell), vascular endothelial cell (e.g. pulmonary artery endothelial cell), adventitial fibroblast, or immune cell (e.g. T lymphocyte, monocyte, macrophage or mast cell). Suitable binding partners include antibodies and the like, directed against cell surface molecules, or ligands or receptors for such cell surface molecules on these cell types. The cell surface molecules may be specific markers for the relevant cell type. Alternatively, the targeting agent may be specifically a binding partner for the 5-HT1B receptor itself.

The term "specific binding pair" is used to describe a pair of molecules comprising a specific binding member (sbm) and a binding partner (bp) therefor which have particular specificity for each other and which in normal conditions bind to each other in preference to binding to other molecules. Examples of specific binding pairs are antibodies and their cognate epitopes/antigens, ligands (such as hormones, etc.) and receptors, avidin/streptavidin and biotin, lectins and carbohydrates, and complementary nucleotide sequences.

It is well known that fragments of a whole antibody can perform the function of binding antigens. Examples of functional binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444-6448, 1993).

As antibodies can be modified in a number of ways, the term "antibody" should therefore be construed as covering any specific binding substance having an binding domain with the required specificity. Thus, this term covers the antibody fragments described above, as well as derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

Alternatives to antibodies are increasingly available. So-called "affinity proteins" or "engineered protein scaffolds" can routinely be tailored for affinity against a particular target. They are typically based on a non-immunoglobulin scaffold protein with a conformationally stable or rigid core, which has been modified to have affinity for the target. Modification may include replacement of one or more surface residues, and/or insertion of one or more residues at the surface of the scaffold protein. For example, a peptide with affinity for the target may be inserted into a surface loop of the scaffold protein or may replace part or all of a surface loop of the scaffold protein. Suitable scaffolds and their engineered equivalents include:

BPTI, LAC-DI, ITI-D2 (Kunitz domain scaffolds);
ETI-II, AGRP (Knottin);
thioredoxin (peptide aptamer);
Fn3 (AdNectin);
lipocalin (BBP) (Anticalin);
ankyrin repeat (DARPin);
Z domain of protein A (Affibody);
gamma-B-crystallin/ubiquitin (Affilin);
LDLR-A-domain (Avimer).

See, for example, Gebauer, M and Skerra, A, Current Op. Chem. Biol. 2009, 13: 245-255, and Friedman, M and Stahl, S, Biotechnol. Appl. Biochem. (2009) 53: 1-29, and references cited therein.

Nucleic Acids Encoding miR-96, Mimics and Precursors

As an alternative to delivering miR-96 oligonucleotides, mimics and precursors directly to a target cell, it is possible to deliver a nucleic acid encoding a miR-96 oligonucleotide, a mimic thereof, or a precursors of either, to the target cell, such that the miR-96 oligonucleotide, mimic or precursor is expressed within the target cell. Such an approach may be regarded as "gene therapy".

It will be readily apparent to the skilled person that nucleic acids can only be used to encode miR-96, mimics and precursors thereof composed of RNA, i.e. composed of the four naturally occurring nucleotide components of RNA, without modified bases, sugars or internucleoside linkages.

The nucleic acid typically comprises an expression construct, comprising a nucleic acid sequence encoding the miR-96 oligonucleotide, mimic or precursor, operably linked with appropriate regulatory sequences to facilitate expression. The regulatory sequences may be selected depending on the target cell, but will typically include an appropriate promoter and optionally an enhancer which direct transcription by RNA polymerase II, as well as a transcriptional terminator (normally including a polyadenylation signal).

The promoter may be a tissue-specific promoter, which drives transcription preferentially or exclusively in the target cell or tissue as compared to other cell or tissue types.

For example, the promoter may be a promoter which drives transcription preferentially or exclusively in vascular cells or in cells associated with the vasculature as defined elsewhere in this specification. Thus the promoter may be active preferentially or exclusively in pulmonary vascular cells, e.g. in vascular smooth muscle cells and/or in vascular epithelial cells (including pulmonary artery smooth muscle cells and epithelial cells), adventitial fibroblasts, or immune cells such as T lymphocytes, mast cells, monocytes and macrophages.

Delivery of Nucleic Acids to Target Cells

Nucleic acids encoding miR-96, mimics and precursors may be delivered by any convenient route.

Methods for delivery of nucleic acid to cells in vitro include calcium phosphate precipitation, DEAE-dextran, electroporation, microinjection, DNA-loaded liposomes, sonication and bombardment using nucleic acid-coated microprojectiles (e.g. gold or tungsten microbeads). Various of these techniques have been successfully adapted for use in vivo or ex vivo.

Thus nucleic acid may be administered in naked form, associated with (e.g. complexed with or encapsulated by) a suitable carrier such as a polymer or lipid (as described elsewhere in this specification), or coated onto a particulate surface. In such embodiments, the nucleic acid is typically DNA. Any of these methods may also be adapted as appropriate for delivery of miR96, precursors and mimics themselves.

The nucleic acid typically takes the form of an expression vector. The skilled person will be capable of designing suitable nucleic acid expression vectors for therapeutic use (as well as for other uses described in this specification). The vectors will typically contain an expression construct comprising the nucleic acid sequence encoding the miR-96, mimic or precursor, in operable linkage with appropriate regulatory sequences, including promoter sequences and transcriptional termination sequences, optionally combined with enhancer sequences, marker genes and other sequences depending upon the particular application. The vectors may be intended to integrate into a host cell chromosome, or may exist and replicate independently of the host chromosomes as an episome, e.g. a plasmid.

Alternatively, a viral vector may be used to deliver the nucleic acid.

Any suitable type of viral vector may be employed as a gene delivery vehicle. These include adenovirus, adeno-associated virus (AAV), retrovirus (especially lentivirus) and herpesvirus vectors. Adenovirus and lentivirus may be particularly preferred as they have the capacity to achieve expression of the gene(s) delivered in cells which are not actively dividing.

The viral vector typically comprises viral structural proteins and a nucleic acid payload which comprises the desired expression construct in a form functional to express the gene in the target cell or tissue. Thus the gene is typically operably linked to a promoter and other appropriate transcriptional regulatory signals.

In adenoviral vectors, the nucleic acid payload is typically a double stranded DNA (dsDNA) molecule. In retroviral vectors, it is typically single stranded RNA.

The nucleic acid payload typically contains further elements required for it to be packaged into the gene delivery vehicle and appropriately processed in the target cell or tissue.

For adenoviral vectors, these may include adenoviral inverted terminal repeat (ITR) sequences and an appropriate packaging signal.

For retroviral vectors, these include characteristic terminal sequences (so-called "R-U5" and "U3-R" sequences) and a packaging signal. The terminal sequences enable the generation of direct repeat sequences ("long terminal repeats" or "LTRs") at either end of the provirus which results from reverse transcription, which then facilitate integration of the provirus into the host cell genome and direct subsequent expression.

The nucleic acid payload may also contain a selectable marker, i.e. a gene encoding a product which allows ready detection of transduced cells. Examples include genes for fluorescent proteins (e.g. GFP), enzymes which produce a visible reaction product (e.g. beta-galactosidase, luciferase) and antibiotic resistance genes.

The viral vector is typically not replication-competent. That is to say, the nucleic acid payload does not contain all of the viral genes (and other genetic elements) necessary for viral replication. The viral vector will nevertheless contain all of the structural proteins and enzyme activities required for introduction of the payload into the host cell and for appropriate processing of the payload such that the encoded miR-96, mimic or precursor can be expressed. Where these are not encoded by the nucleic acid payload, they will typically be supplied by a packaging cell line. The skilled person will be well aware of suitable cell lines which can be used to generate appropriate viral delivery vehicles.

Thus, for an adenoviral vector, the nucleic acid payload typically lacks one or more functional adenoviral genes from the E1, E2, E3 or E4 regions. These genes may be deleted or otherwise inactivated, e.g. by insertion of a transcription unit comprising the heterologous gene or a selective marker.

In some embodiments, the nucleic acid contains no functional viral genes. Thus, for an adenoviral vector, the only viral components present may be the ITRs and packaging signal.

Nucleic acids having no functional viral genes may be preferred, as they reduce the risk of a host immune response developing against the transduced target cell or tissue as a result of viral protein synthesis.

Subjects for Treatment

The methods of the invention may be used for treatment or prophylaxis of pulmonary arterial hypertension (PAH). Prophylactic use does not necessarily imply complete prevention of the disease, but encompasses delaying onset of disease and/or reducing the severity of symptoms, whether at onset or afterwards. Thus subjects may suffer from, or may be at risk of developing, PAH.

Pulmonary arterial hypertension involves vasoconstriction of the blood vessels to and within the lungs. It is characterised by severe pulmonary arterial remodelling and occlusive pulmonary vascular lesions, leading to right ventricular failure. It is a significant cause of mortality in patients with systemic lupus erythematosus (SLE). The invention thus encompasses methods of prophylaxis or treatment of PAH in SLE patients, as well as in patients unaffected by SLE.

PAH includes idiopathic PAH and heritable PAH (also known as familial PAH). Thus the subject may have a mutation which pre-disposes them to developing PAH. For example, this may be a mutation in the BMPR2 gene (type II receptor for the bone morphogenetic protein pathway). Such mutations include R899X which introduces a premature stop codon and N903S. Other pre-disposing mutations include loss-of-function mutations in the KCNK3 gene (potassium channel sub-family K, member 3).

The subjects may previously have been tested for a genetic pre-disposition to PAH. The invention also provides a method of prophylaxis or treatment of PAH comprising determining the presence or absence of a genetic predisposition to PAH in a subject's genome and, if such a predisposition is identified, prescribing or administering to the subject:
(a) miR-96, a mimic thereof, or a precursor of either; or
(b) a nucleic acid encoding miR-96, a mimic thereof, or a precursor of either.

The subjects may be suffering from or at risk of developing idiopathic PAH. Known risk factors include female gender, and a history of taking anorectic medication such as fenfluramine/phentermine ("fen-phen").

The invention may be particularly applicable to treatment of female subjects but treatment of male subjects may also be beneficial and is encompassed within the scope of the invention.

Although the most common subjects for treatment will be humans, the methods of the invention may extend to any other mammals, including other primates (especially great apes such as gorilla, chimpanzee and orang utan, but also Old World and New World monkeys) as well as rodents (including mice and rats), and other common laboratory, domestic and agricultural animals (including but not limited to rabbits, dogs, cats, horses, cows, sheep, goats, etc.).

Pharmaceutical Compositions and Methods of Treatment

The molecules described herein can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular and intraperitoneal routes. Examples of suitable compositions and methods of administration are provided in Esseku and Adeyeye (2011) and Van den Mooter G. (2006).

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whatever the nature of the active agent that is to be given to an individual (e.g. a cell, polypeptide, nucleic acid molecule, other pharmaceutically useful agent according to the present invention), administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The invention will now be described in more detail, by way of example and not limitation, by reference to the accompanying drawings and examples.

Analysis of microRNA expression by quantitative-PCR in female and male WT and BMPR2$^{R899X+/-}$ PASMCs show gender can affect expression profile. Results are normalized to U6 and expressed as a fold change of female WT value. Data expressed as mean±SEM. P<0.05*, p<0.01** (female vs. male) and p<0.05$^+$, p<0.01$^{++}$, p<0.001$^{+++}$ (WT vs. BMPR2$^{R899X+/-}$).

Figure 2:
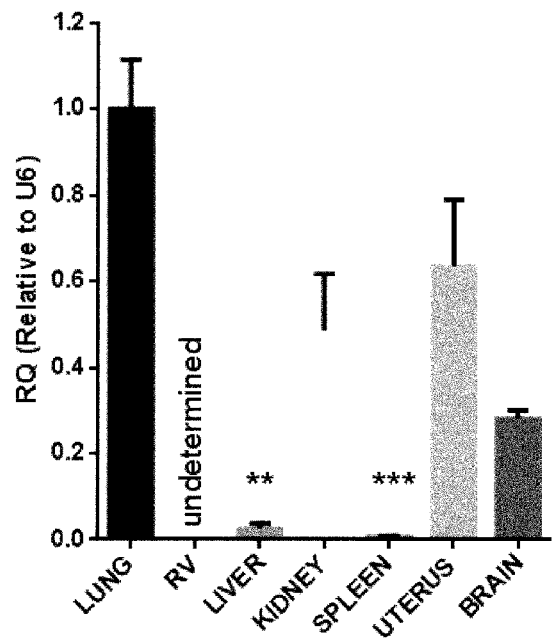

FIG. 2. Expression of miR-96 highest in lung

Global analysis of miR-96 expression by quantitative-PCR in mouse tissue shows levels are significantly higher in lung. (RV, Right Ventricle). Results are normalized to U6 and expressed as a fold change of lung value. Data expressed as mean±SEM. P<0.01 and P<0.001*.

Figure 3:
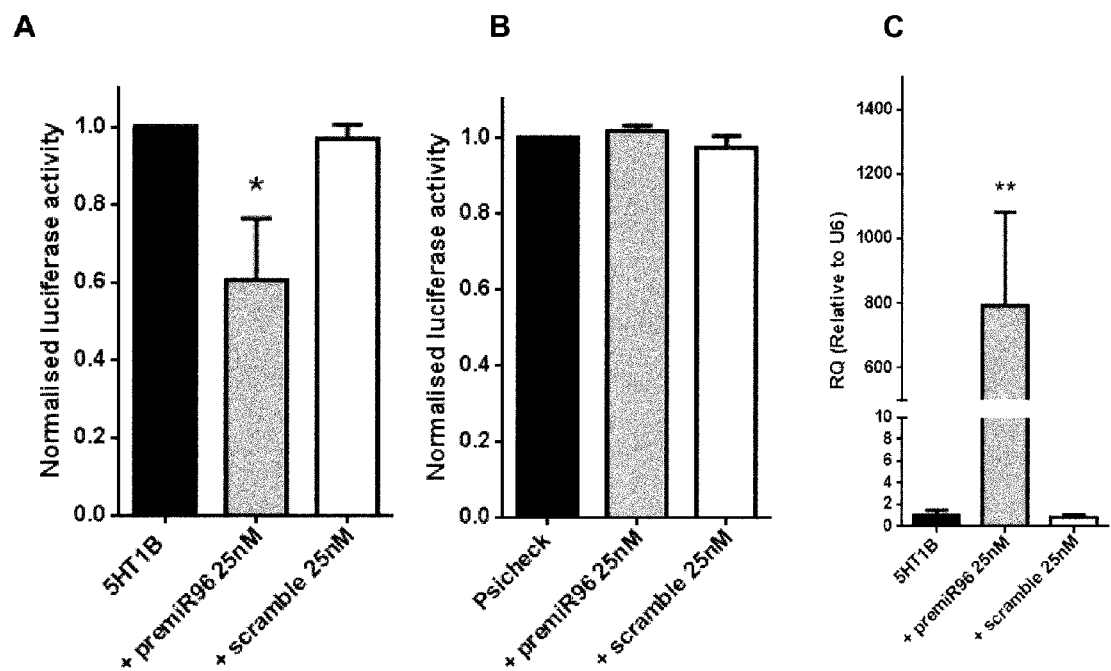

FIG. 3. Validation of the 5-HT1B receptor as a target of miR-96

(A) and (B) Pre-miR-96 at concentration of 25 nM decreases luciferase activity but has not effect on mock control vector. (C) Pre-miR-96 transfection increases mature miR-96 levels compared to control and scrambled miR. Results were normalised to U6 and expressed as a fold change of control value. Data expressed as mean±SEM. P<0.05* and P<0.01**.

Figure 4:
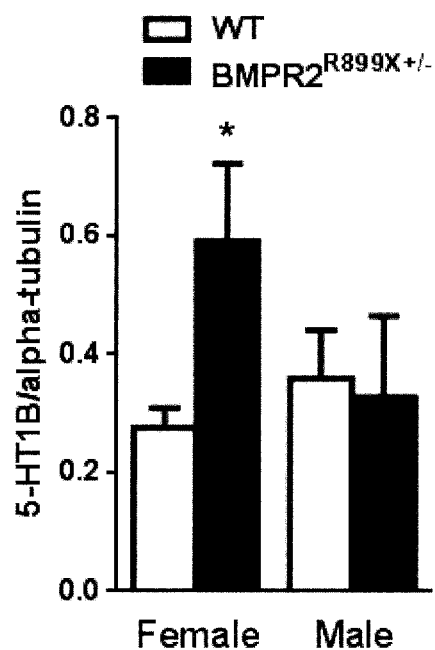
Figure 4:
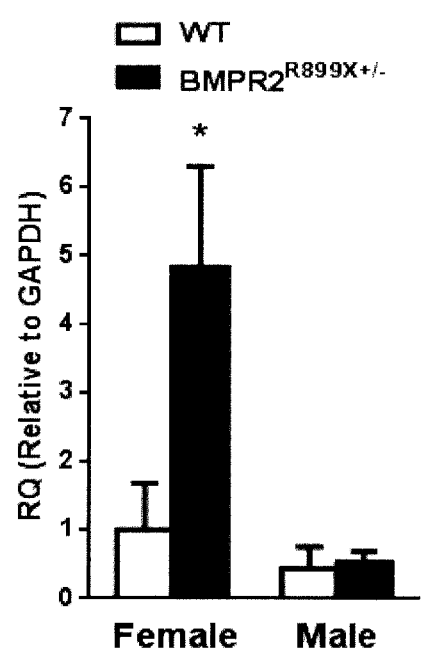
Figure 4:
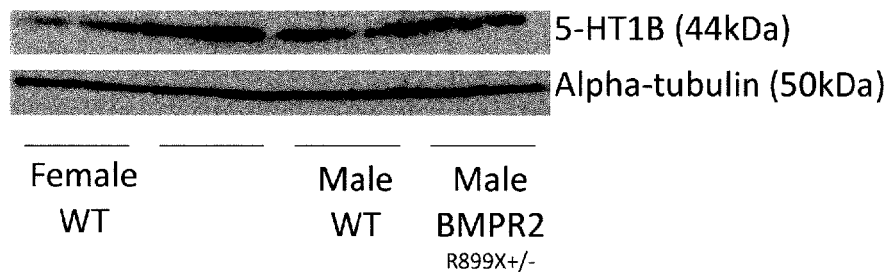

FIG. 4. Increased expression of target 5-HT1B in female BMPR2$^{R899X+/-}$ PASMCs Analysis of 5-HT1B (A) protein and (B) mRNA expression in female and male PASMCs from WT and BMPR2$^{R899X+/-}$ mice. Female BMPR2$^{R899X+/-}$ PASMCs exhibit increased 5-HT1B protein and mRNA expression compared to female WT. Representative immunoblot of 5-HT1B protein expression in mouse PASMCs (C). Results were normalised to alpha-tubulin and GAPDH respectively and expressed as a fold change. Data expressed as mean±SEM. P<0.05*, p<0.01** (female vs. male) and p<0.05$^+$, p<0.01$^{++}$, p<0.001$^{+++}$ (WT vs. +/−).

Figure 5:
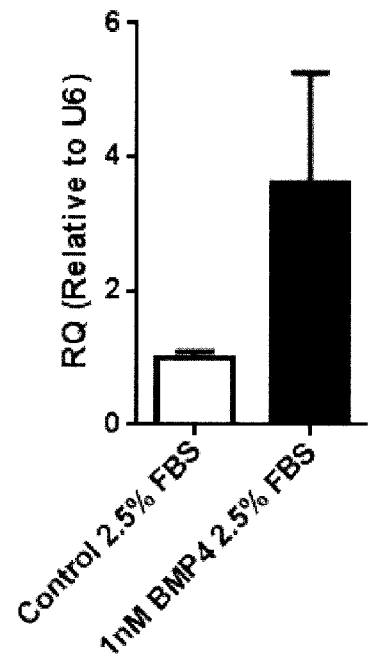

FIG. 5. BMP4 stimulation rescues miR-96 expression in deficient female BMPR2$^{R899X+/-}$ PASMCs Mouse PASMCs from female BMPR2$^{R899X+/-}$ mice exhibit a tentative increase in miR-96 levels when stimulated with 1 nM BMP4. Results were normalised to U6 and expressed as a fold change. Data expressed as mean±SEM.

Figure 6:
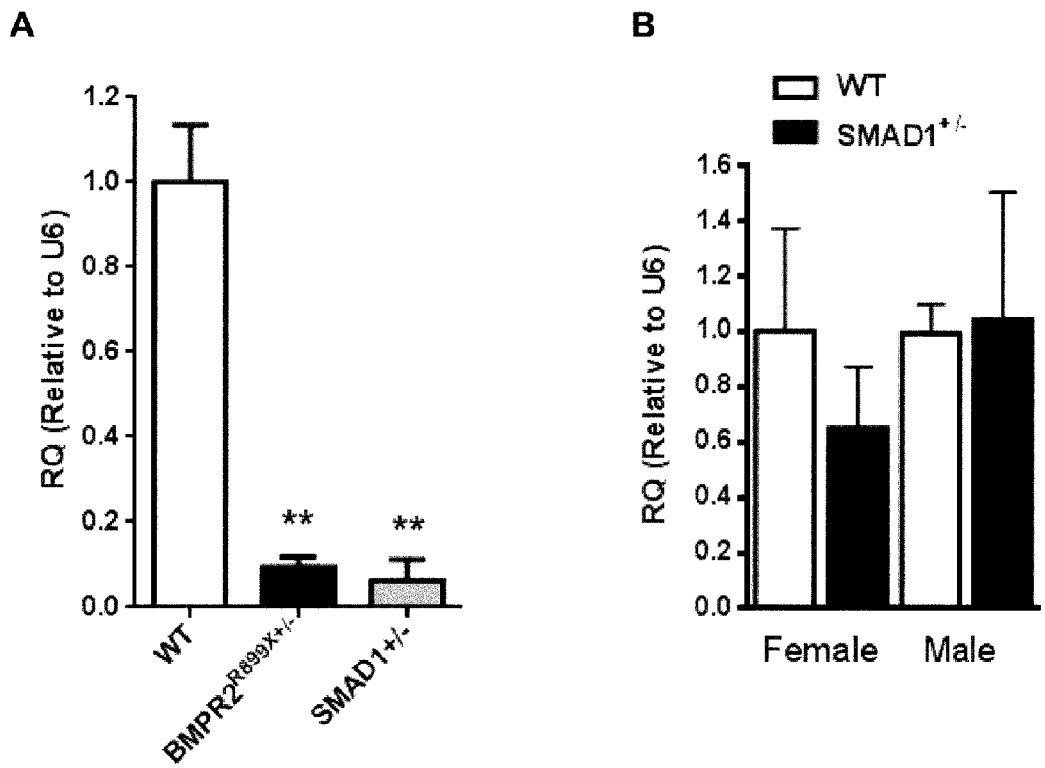

FIG. 6. Deficiency of SMAD1 exhibits similar miR-96 expression profile as BMPR2$^{R899X+/-}$ Mouse PASMCs from female mice with compromised SMAD1 expression (+/−) show a reduction in miR-96 expression compared to female WT (A). In whole lung tissue there is a trend for a decrease in miR-96 levels in female SMAD1+/− mice vs. female WT with no change between males (B). Results were normalised to U6 and expressed as a fold change. Data expressed as mean±SEM. P<0.01**.

Figure 7:
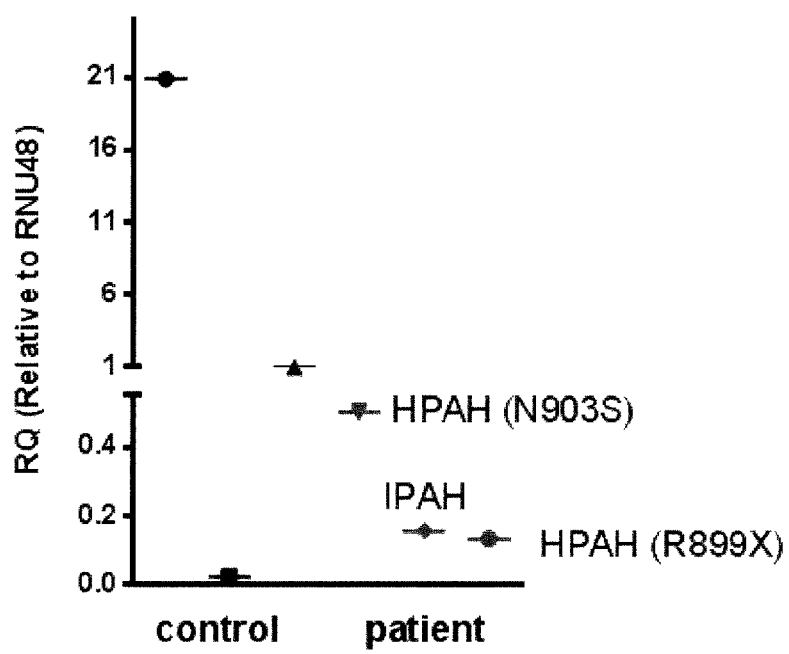
Figure 7:
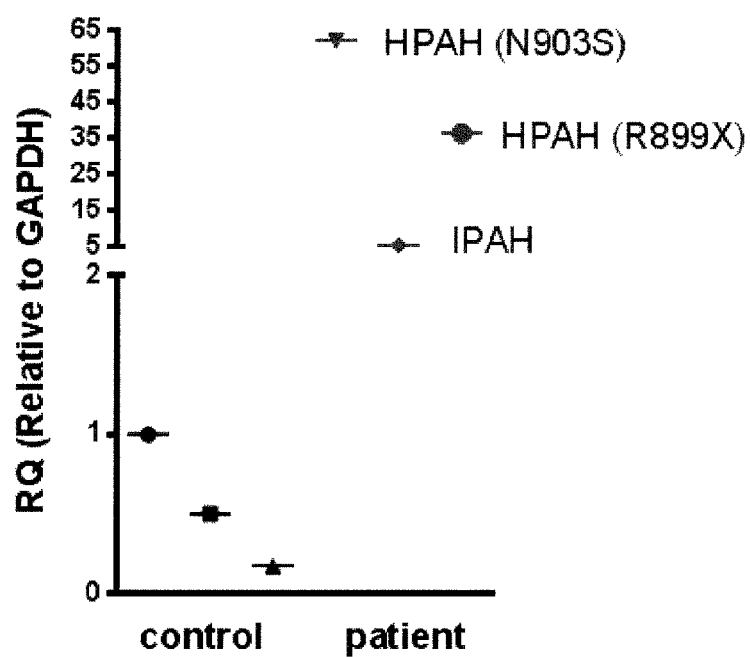

FIG. 7. Effect of Human PAH on miR-96 and 5-HT1B Expression

Female patient PASMCs have a reduction in mir-96 expression compared to non-PAH controls (A). The 5-HT1B receptor expression is increased in female patient PASMCs compared to non-PAH controls (B), low expression of miR-96 and high expression of 5-HT1B is found within HPAH patients with BMPR2 mutations. Results were normalised to RNU48 and expressed as a fold change of female control value. Data expressed as mean. R899X, N903S: BMPR2 mutations. HPAH: heritable PAH. IPAH: idiopathic PAH.

Figure 8:
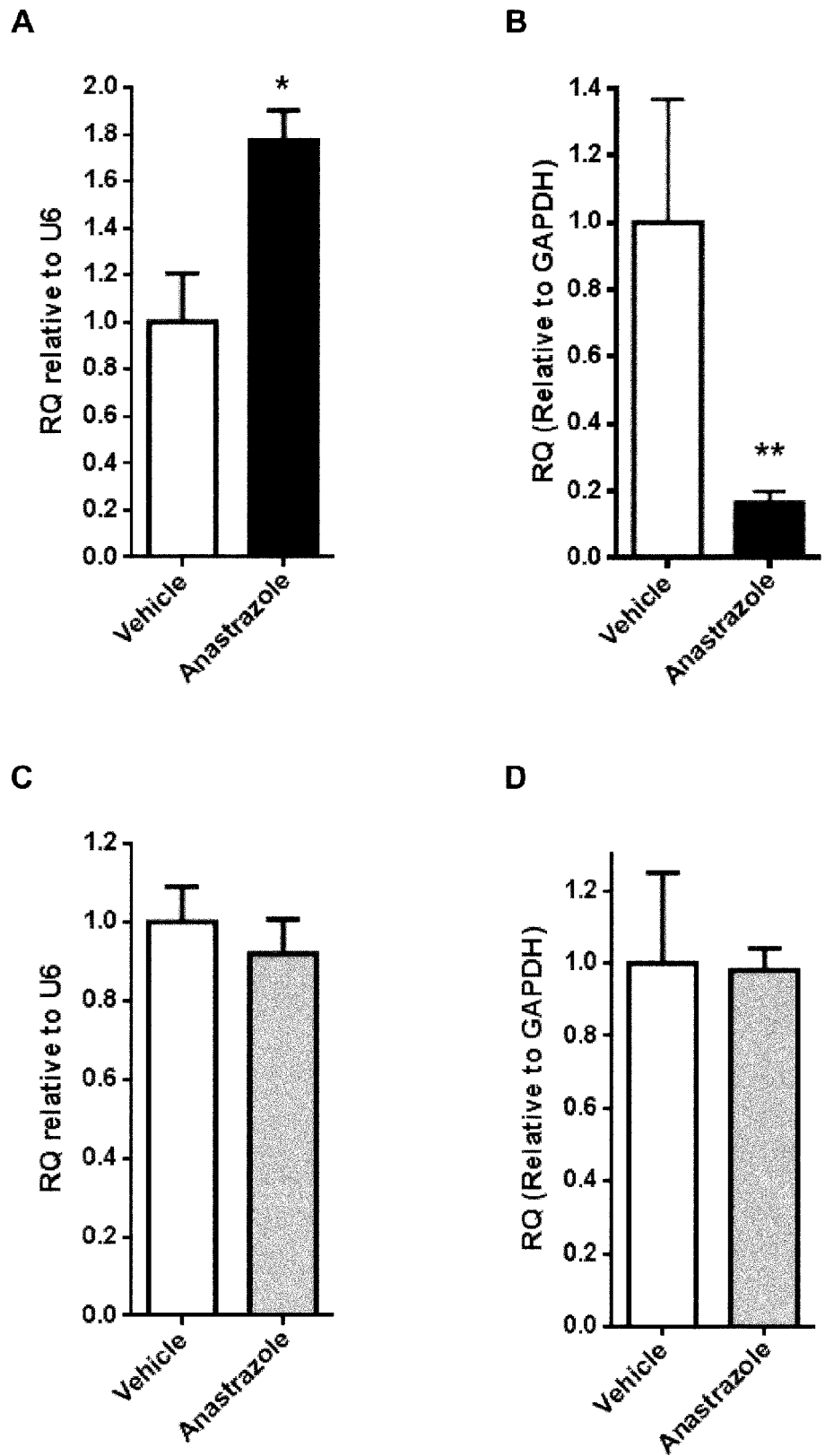

FIG. 8. Depletion of oestrogen increases miR-96 expression and decreases target 5-HT1B only in female mice Female mice treated with the aromatase inhibitor, anastrazole, have an increased expression of miR-96 (A) and decreased expression of 5-HT1B (B) compared to vehicle control whereas male mice exhibit no change in expression of either miR-96 (C) or 5-HT1B (D). Results were normalised to U6 and expressed as a fold change of control value. Data expressed as mean±SEM. P<0.05* and P<0.01**.

Figure 9:
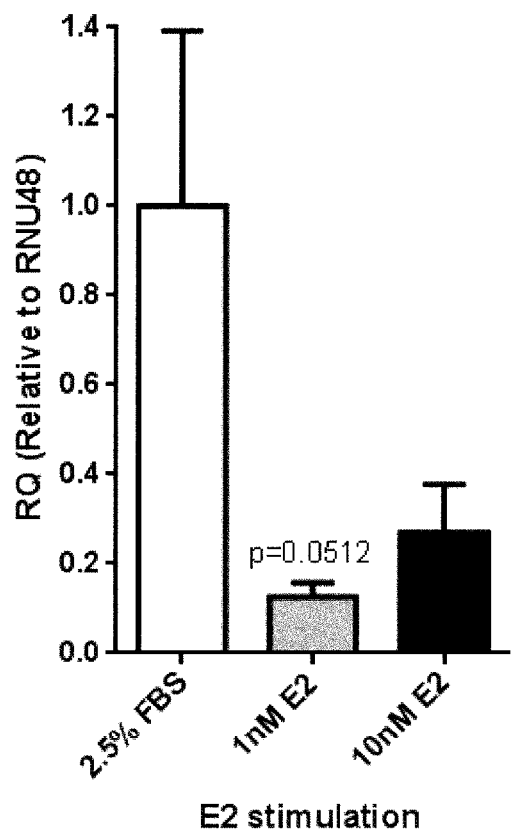
Figure 9:
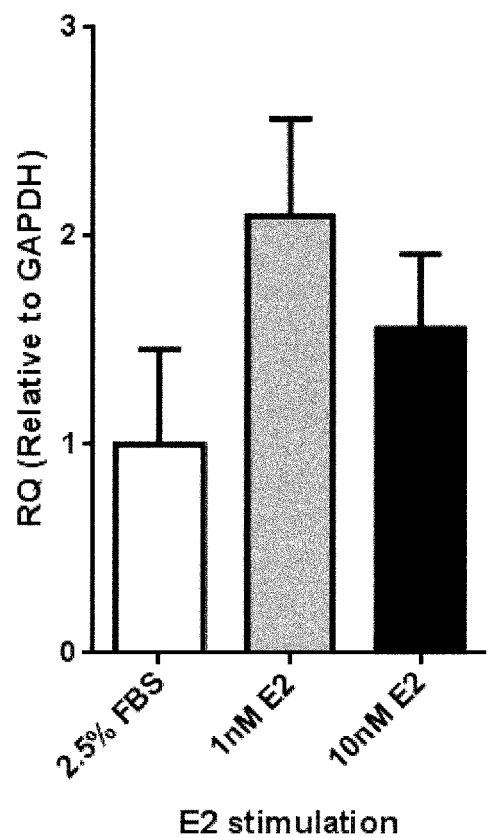

FIG. 9. A Role for oestrogen in the regulation of miR-96

Human PASMCs stimulated with 1 nM oestrogen (E2) for 72 hours show a reduction in miR-96 expression (p=0.0512) (A) and a corresponding trend for an increase in 5-HT1B receptor expression (B). Results were normalised to RNU48 and expressed as a fold change of control value. Data expressed as mean±SEM.

Figure 10:
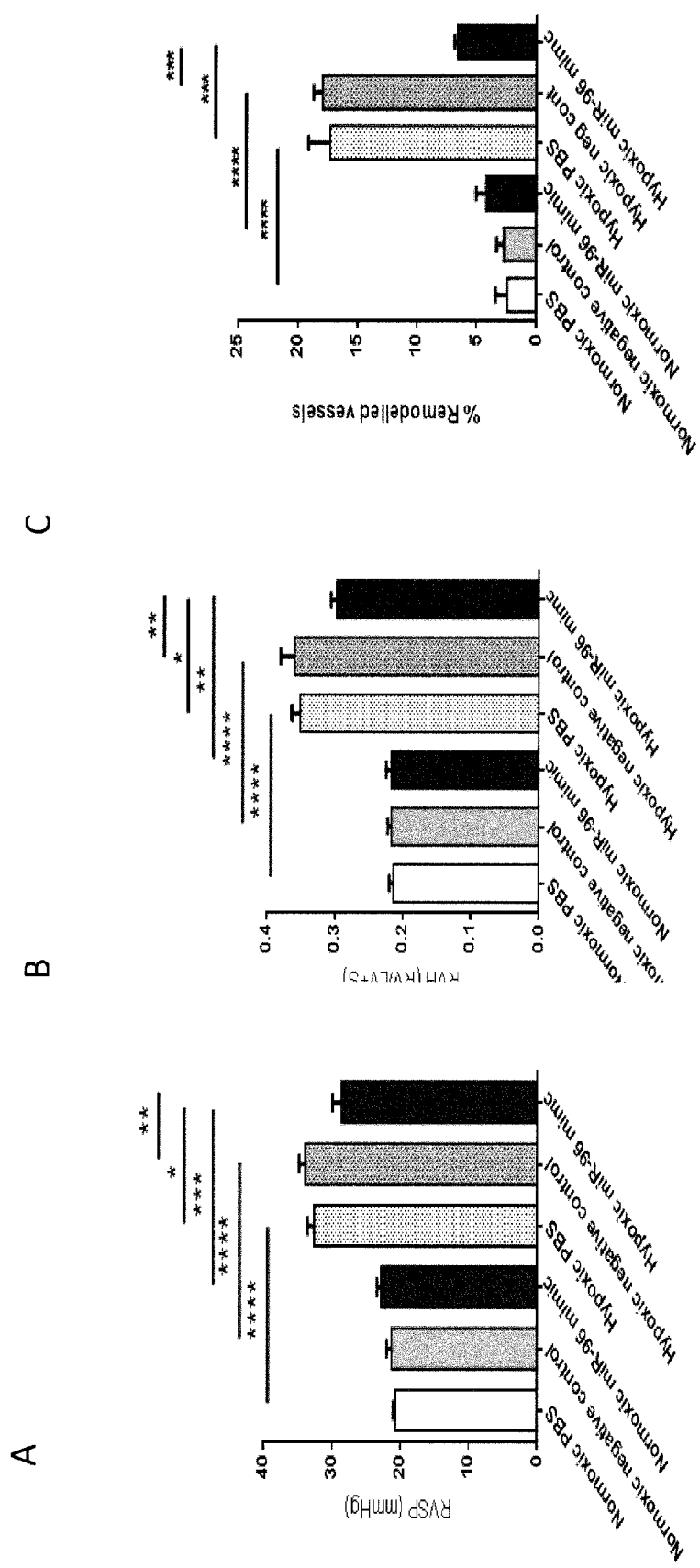

FIG. 10. A mir-96 mimic prevents hypoxia-induced pulmonary hypertension (PH) in the mouse. 1.5 mg/kg of the mir-96 mimic was administered i.v. once a week for two weeks during which time mice were exposed to hypoxia. The miR-96 mimic prevents the rise in Right ventricular Systolic pressure (A), right ventricular hypertrophy (B) and pulmonary vascular remodeling (C). *P<0.05, P<0.01, P<0.001, ****P<0.0001; 1-way ANOVA followed by Tukey's post-hoc test.

Figure 11:
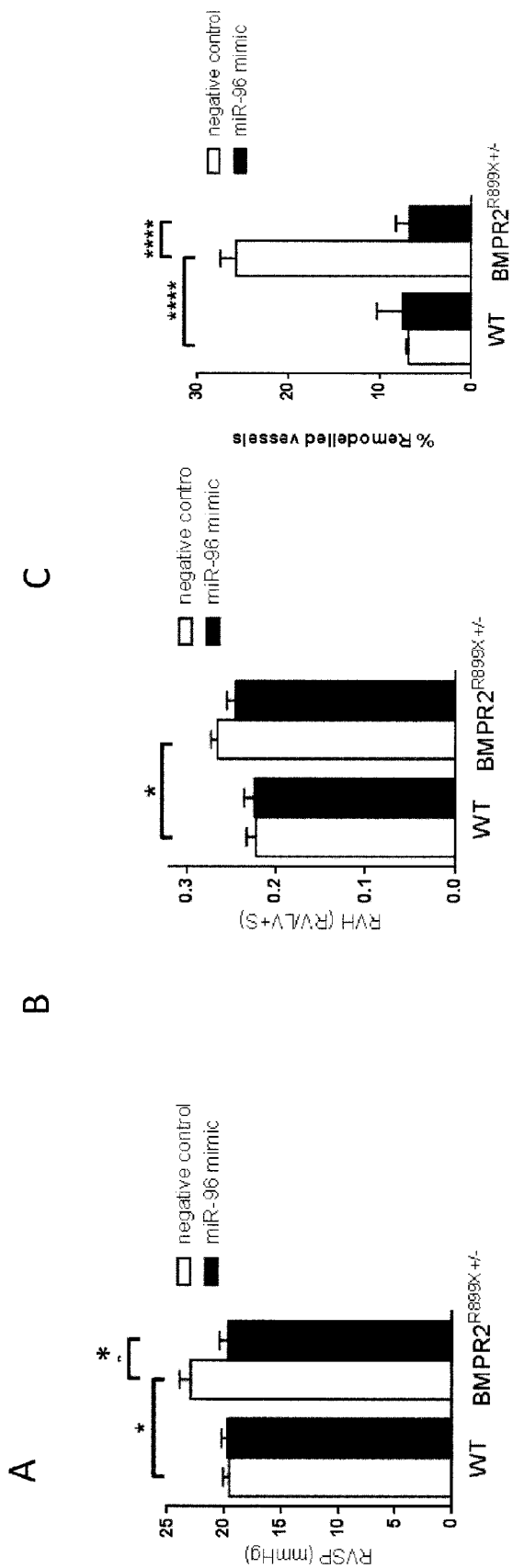

FIG. 11. A mir-96 mimic reverses pulmonary hypertension (PH) in a mouse with a BMPR2 mutation (BMPR2$^{R899X+/-}$). 1.5 mg/kg of the mir-96 mimic was administered i.v. once a week for two weeks after which the mice were assessed for the development of PH. The miR-96 mimic prevents the rise in Right Ventricular Systolic pressure (A), right ventricular hypertrophy (B) and pulmonary vascular remodeling (C).*P<0.05,*P<0.001, **P<0.0001; 1-way ANOVA followed by Tukey's post-hoc test

DETAILED DESCRIPTION OF THE INVENTION

Research suggests that microRNAs (miRs) play a crucial role in the pathobiology of pulmonary arterial hypertension (PAH).

Heritable PAH (hPAH) is associated with mutations in the gene for bone morphogenetic protein receptor 2 (BMPR2). The inventors have studied a BMPR2 mouse model of PAH carrying a mutation also found in PAH patients, the BMPR2$^{R899X+/-}$ mouse.

In this model, gender emerges as a key underlying regulator of basal expression of miRs within pulmonary artery smooth muscle cells (PASMCs). MiR-96 was down-regulated in PASMCs from female BMPR2$^{R899X+/-}$ mice compared to the female wild type (WT) whereas expression between the male transgenics and their WT controls was unchanged. Global expression analysis showed highest miR-96 expression within the lung. The target gene for the 5-HT1B receptor was inversely correlated with the expression of miR-96 within the female BMPR2$^{R899X+/-}$ PASMCs at both mRNA and protein level. The 5HT1B gene was validated as a target for miR-96 by luciferase reporter assay.

The inventors also verified that PASMC from female PAH patients with BMPR2 mutations exhibit low miR-96 and high 5HT1B expression.

These results suggest sex hormones such as oestrogen may play a role in regulating miR-96. Consistent with this we have shown that inhibiting the synthesis of endogenous oestrogen in vivo increased lung miR-96 and decrease 5-HT1B expression within female mice only. Direct stimulation with oestrogen in human PASMCs caused a reduction in miR-96 and increase in 5-HT1B expression.

In summary, a decrease in miR-96 was associated with increased 5HT1B expression. This suggests that miR-96 mimic/pre-miR-96 strategies may be a novel therapeutic approach to PAH. In support of this hypothesis, pre-clinical studies confirm that a mir-96 mimic is effective in preventing or reversing pulmonary hypertension in mouse models of pulmonary hypertension.

EXAMPLES

Materials and Methods
Cell Culture
Murine Pulmonary Artery Smooth Muscle Cells

Female and male pulmonary artery smooth muscle cells (PASMCs) derived from BMPR2$^{+/-R899X}$ mice and corresponding wild type control mice were provided by Prof. N. W. Morrell (University of Cambridge, Cambridge, UK). BMPR2$^{+/-R899X}$ mice have a heterozygous knock-in mutation of the BMPR2 gene. The mice were similar to those described by West et al. (Am J Physiol Lung Cell Mol Physiol 295: L744-L755, 2008). Briefly PAMSCs were grown in 20% FBS (Foetal Bovine Serum) DMEM (Dulbecco's Modified Eagle Medium) in the presence of growth factors (epidermal growth factor, basic fibroblast growth factor and insulin) and antibiotic (Penicillin Streptomycin). PASMCs were utilised between passage 4 and 8 and cell viability was based on distinct smooth muscle cell morphology.

Human Pulmonary Artery Smooth Muscle Cells

Female human PASMCs were provided by Prof. N. W. Morrell (University of Cambridge, Cambridge, UK). Briefly human PASMCs were explanted from the small distal pulmonary arteries of the pulmonary vasculature from three PAH patients, two with HPAH and one with IPAH. PASMCs derived from non-PAH subjects were utilised as controls. Human PASMCs were grown in 10% FBS DMEM in the presence of antibiotic antimycotic solution (containing penicillin, streptomycin and amphotericin) and were used between passage 4 and 8. PASMC phenotype was confirmed via smooth muscle cell morphology.

RNA and Protein Analysis
Taqman Quantitative-PCR Analysis of miRNAs and mRNAs

Total RNA was extracted using the miRNeasy kit (Qiagen) according to the manufacturer's instructions and RNA purity quantified using NanoDrop-1000 Spectrophotometer. Expression of miRs and mRNA was assessed by Taqman quantitative-PCR as previously described [17]. To obtain a fold change miR expression data was normalised to U6 for mouse and RNU48 for human. mRNA expression data was normalised to GAPDH. All PASMC miRNA and mRNA expression data is n=6 in triplicate.

Western Blot Analysis of Protein

Protein was extracted using the RIPA lysis method. The RIPA buffer was supplemented with proteases inhibitors PMSF, soybean trypsin inhibitor and benzamidine. Briefly supplemented RIPA buffer was added to PASMCs which were then agitated on ice for 10 minutes. Cell lysates were collected via scraping. Protein expression data was normalised to alpha-tubulin and quantified using densitometry. All protein expression data is n=4 in duplicate.

Effectiveness of microRNA-96 Mimic In Vivo

To assess whether miR-96 was involved in the pathology of pulmonary hypertension, the microRNA-96 mimic (Applied Biosystems, #MC10422, having the base sequence

UUUGGCACUAGCACAUUUUUGCU,    (SEQ ID NO: 1)

identical to mature mouse and human miR-96) was administered intravenously via the tail vein once a week for 2 weeks using the MaxSuppressor™ In Vivo RNA-LANCEr II delivery method. The mimic was prepared in the delivery reagent as per manufacturing instructions at a dose of 1.5 mg/kg per injection i.e. ~30 ug per mouse per injection. Negative microRNA mimic (Applied Biosystems) and PBS dosed animals were used as controls.

Chronic Hypoxia

Female wild type (WT) C57/Bl (Charles River) mice aged 2 months old were exposed to 14 day hypobaric hypoxia (10% $O_2$, 550 mbar) as described previously (18). Mice maintained in normoxic conditions (21% $O_2$, 1000 mbar) were studied as controls.

In Vivo Assessment of PH

Measurements of right ventricular systolic pressure (RVSP), right ventricular hypertrophy (RVH) and pulmonary vascular remodeling were performed as previously described (3,4,10)

Target Validation

Luicferase Reporter Assay

The psi-CHECK-2 dual luciferase reporter vector (Promega) was utilised for the reporter assay. Briefly, a fragment of the 3'UTR (untranslated region) of the 5-HT1B receptor gene was generated by polymerase chain reaction (PCR) from genomic mouse DNA and was cloned via the in-fusion cloning method into the multiple cloning site of the psi-CHECK-2 vector at the XhoI and the NotI restriction sites. The psi-CHECK-2 5-HT1B vector was then sequenced to confirm there was no unwanted mutations within the 3'UTR region of the 5-HT1B. lug of psi-CHECK-2 control vector or the psi-CHECK-2 5HT1B vector along with either pre-miR-96 (Ambion) or scrambled miR (Ambion) were co-transfected into HeLa cells using Lipofectamine 2000 (Invitrogen) and optimem (Invitrogen) for a total of 6 hours before being replaced with 10% FBS DMEM. The HeLa cells were left for 48 hours and the luciferase activity measured using the Dual-Glo Luciferase Assay System (Promega) and detected by a luminometer. The *renilla* luciferase activity was normalised to the internal firefly luciferase activity and data expressed as a percentage of the internal control.

Analysis of Data

Values are expressed as mean±standard error of the mean. A t-test or 2-way ANOVA followed by Bonferroni's post-hoc test was performed to evaluate the statistical significance between all groups where appropriate. A probability level of $p<0.05$ was defined as being statistically significant.

Results

Figure 1:
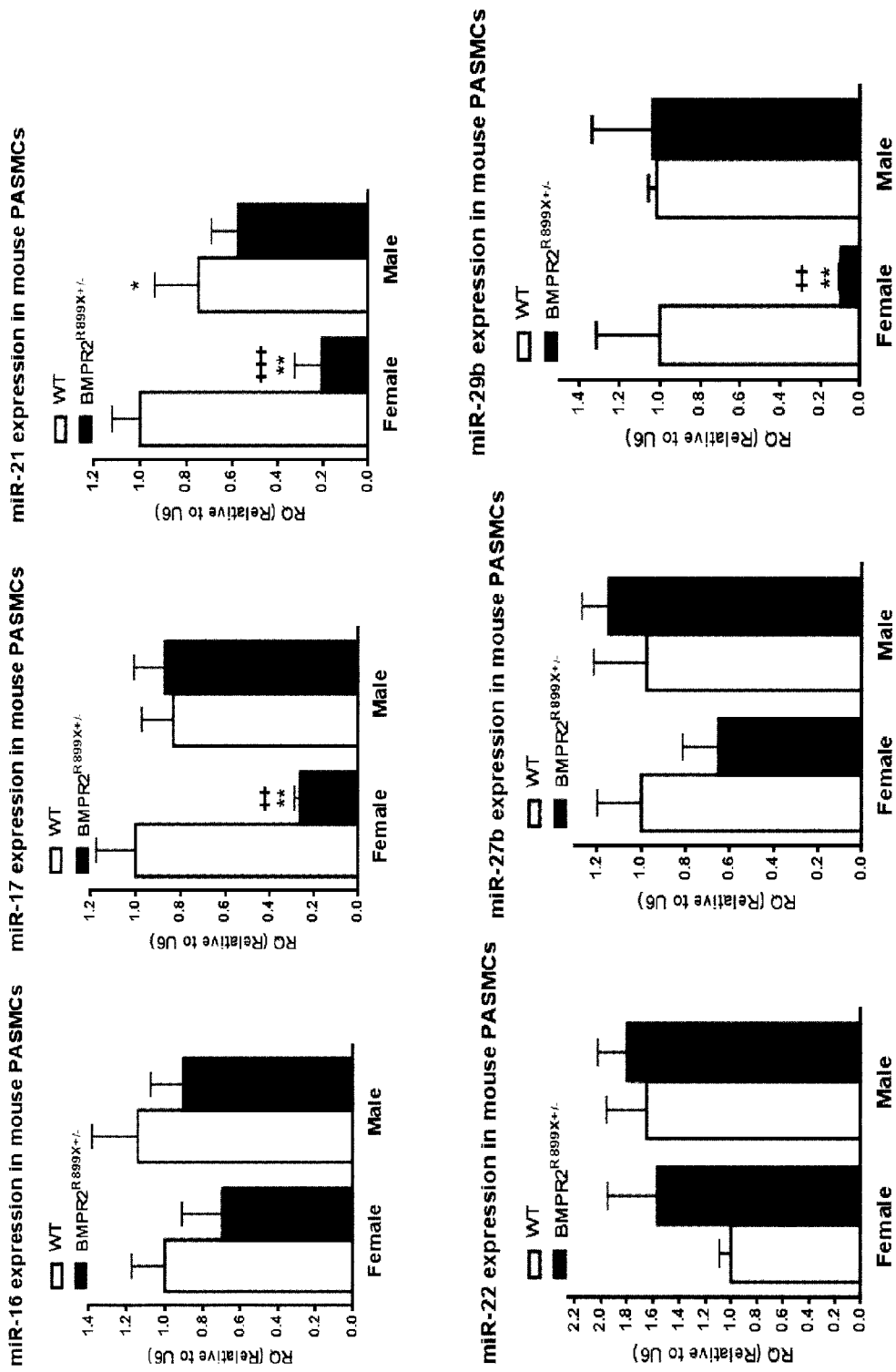
FIG. 1: Differential expression of microRNAs across genders in PASMCs

FIG. 1 demonstrates that many miRs were differentially affected by gender, and miR-96 was severely down regulated in female $BMPR2^{R899X+/-}$ mice vs wild type controls but not males; miR-96 levels were lower in female $BMPR2^{R899X+/-}$ mice vs male $BMPR2^{R899X+/-}$ mice.

Lung expression of miR-96 is extremely high compared with other tissue levels which would facilitate selective targeting of the lung (FIG. 2). We confirmed that the 5HT1B receptor is a target for miR96 using luciferase reporter assay (FIG. 3).

Decreased expression of miR96 was associated with an elevation in the target gene for the 5HT1B receptor in the female $BMPR2^{R899X+/-}$ mice (FIG. 4). The decreased miR96 expression was rescued by BMP4 stimulation (FIG. 5). The same phenotype is observed in PASMCs from Smad1+/- mice (FIG. 6).

Results have been confirmed in human PASMCs (FIG. 7). Of especial interest is that in a female patient with the R899X mutation, 5HT1B levels were high and miR96 expression extremely low (FIG. 7).

We also examined the effect of oestrogen depletion with an aromatase inhibitor, anastrozole on the expression of both miR96 and the 5HT1B receptor. Previously we have shown that anastrozole reverses PAH in female mice and rats but not in males (unpublished). Here we show that depletion of oestrogen in vivo with anastrozole increased miR96 expression and decreased 5HT1B expression in the female mouse lung but not the male (FIG. 8).

In keeping with this, the miR-96 gene has oestrogen-responsive regions and oestrogen itself decreased expression of miR-96 and increased expression of the 5HT1B receptor in (FIG. 9).

FIGS. 10 and 11 confirm that a miR-96 mimic can both prevent and reverse experimental PH in a mouse model in vivo.

Discussion

Our results suggest that increased oestrogen and BMPR2 haploinsufficiency are associated with decreased miR-96 expression.

miR-96 normally represses the translation of the gene for 5HT1B and so the decrease in miR-96 induces an increase in 5HT1B expression. This facilitates PASMC proliferation by serotonin and pulmonary vascular remodelling and contributes to the development of PAH.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

REFERENCES (1) Shapiro S, Traiger G L, Turner M, Mcgoon M D, Wason P, Barst R J. Sex differences in the diagnosis, treatment, and outcome of patients with pulmonary arterial hypertension enrolled in the registry to evaluate early and (1) long-term pulmonary arterial hypertension disease management. *Chest* 2012 February; 141(2):363-73.
(2) Lane K B, Machado R D, Pauciulo M W et al. Heterozygous germline mutations in BMPR2, encoding a TGF-beta receptor, cause familial primary pulmonary hypertension. *Nature Genetics* 2000 September; 26(1):81-4.
(3) Dempsie Y, Morecroft I, Welsh D J et al. Converging evidence in support of the serotonin hypothesis of dexfenfluramine-induced pulmonary hypertension with novel transgenic mice. *Circulation* 2008 Jun. 3; 117(22):2928-37.
(4) Morecroft I, Dempsie Y, Bader M et al. Effect of Tryptophan Hydroxylase 1 Deficiency on the Development of Hypoxia-Induced Pulmonary Hypertension. *Hypertension* 2007 Jan. 1; 49(1):232-6.
(5) Morecroft I, White K, Caruso P et al. Gene Therapy by Targeted Adenovirus-mediated Knockdown of Pulmonary Endothelial Tph1 Attenuates Hypoxia-induced Pulmonary Hypertension. *Mol Ther* 2012 August; 20(8):1516-28.
(6) Lawrie A, Spiekerkoetter E, Martinez E C et al. Interdependent serotonin transporter and receptor pathways regulate S100A4/Mts1, a gene associated with pulmonary vascular disease. *Circ Res* 2005 Aug. 5; 97(3):227-35.
(7) MacIntyre P D, Bhargava B, Hogg K J, Gemmill J D, Hillis W S. Effect of Subcutaneous Sumatriptan, A Selective 5Ht1 Agonist, on the Systemic, Pulmonary, and Coronary Circulation. *Circulation* 1993 February; 87(2): 401-5.
(8) MacLean M R, Clayton R A, Templeton A G B, Morecroft I. Evidence for 5-HT1-like receptor-mediated vasoconstriction in human pulmonary artery. *British Journal of Pharmacology* 1996 September; 119(2):277-82.
(9) MacLean M R, Morecroft I. Increased contractile response to 5-hydroxytryptamine(1)-receptor stimulation in pulmonary arteries from chronic hypoxic rats: role of pharmacological synergy. *British Journal of Pharmacology* 2001 October; 134(3):614-20.
(10) MacLean M R, Deuchar G A, Hicks M N et al. Overexpression of the 5-hydroxytryptamine transporter gene—Effect on pulmonary hemodynamics and hypoxia-induced pulmonary hypertension. *Circulation* 2004 May 4; 109(17):2150-5.
(11) Morecroft I, Heeley R P, Prentice H M, Kirk A, MacLean M R. 5-hydroxytryptamine receptors mediating contraction in human small muscular pulmonary arteries: importance of the 5-HT1B receptor. *British Journal of Pharmacology* 1999 October; 128(3):730-4.
(12) Morecroft I, Loughlin L, Nilsen M et al. Functional interactions between 5-hydroxytryptamine receptors and the serotonin transporter in pulmonary arteries. *J Pharmacol Exp Ther* 2005 May; 313(2):539-48.
(13) Morecroft I, Pang L, Baranowska M et al. In vivo effects of a combined 5-HT(1B) receptor/SERT antagonist in experimental pulmonary hypertension. *Cardiovasc Res* 2010 Feb. 1; 85(3):593-603.
(14) Dempsie Y, Nilsen M, White K et al. Development of pulmonary arterial hypertension in mice over-expressing S100A4/Mts1 is specific to females. *Respiratory Research* 2011; 12(1):159.
(15) Dempsie Y, MacRitchie N A, White K et al. Dexfenfluramine and the oestrogen-metabolizing enzyme CYP1B1 in the development of pulmonary arterial hypertension. *Cardiovasc Res* 2013 Jul. 1; 99(1):24-34.
(16) White K, Dempsie Y, Nilsen M, Wright A F, Loughlin L, MacLean M R. The serotonin transporter, gender, and 17 beta oestradiol in the development of pulmonary arterial hypertension. *Cardiovasc Res* 2011 May; 90(2): 373-82.
(17) White K, Loughlin L, Maqbool Z et al. Serotonin transporter, sex, and hypoxia: microarray analysis in the pulmonary arteries of mice identifies genes with relevance to human PAH. *Physiological Genomics* 2011 April; 43(8):417-37.
(18) Caruso P, MacLean M R, Khanin R et al. Dynamic Changes in Lung MicroRNA Profiles During the Development of Pulmonary Hypertension due to Chronic Hypoxia and Monocrotaline. *Arteriosclerosis Thrombosis and Vascular Biology* 2010 April; 30(4):716-U182.
(19) Caruso P, Dempsie Y, Stevens H C et al. A Role for miR-145 in Pulmonary Arterial Hypertension/Novelty and Significance. *Circ Res* 2012 Jul. 20; 111(3):290-300.
(20) Grant J, White K, MacLean M, Baker A. MicroRNAs in pulmonary arterial remodeling. *Cell Mol Life Sci* 2013; 1-16.
(21) Bouchie A. First microRNA mimic enters clinic. *Nat Biotechnol* 2013 Jul. 9; 31(7):577.
(22) Stefulj J, Jernej B, Cicin-Sain L, Rinner I, Schauenstein K. mRNA expression of serotonin receptors in cells of the immune tissues of the rat. *Brain Behav Immun* 2000 September; 14(3):219-24.
(23) Yang G B, Qiu C L, Zhao H, Liu Q, Shao Y. Expression of mRNA for multiple serotonin (5-HT) receptor types/subtypes by the peripheral blood mononuclear cells of rhesus macaques. *J Neuroimmunol* 2006 September; 178 (1-2):24-9.
(24) Yin J, Albert R H, Tretiakova A P, Jameson B A. 5-HT1B receptors play a prominent role in the proliferation of T-lymphocytes. *Journal of Neuroimmunology* 2006 December; 181(1-2):68-81.
(25) Austin E D, Rock M T, Mosse C A et al. T lymphocyte subset abnormalities in the blood and lung in pulmonary arterial hypertension. *Respir Med* 2010 March; 104(3): 454-62.
(26) Savai R, Pullamsetti S S, Kolbe J et al. Immune and inflammatory cell involvement in the pathology of idiopathic pulmonary arterial hypertension. *Am J Respir Crit Care Med* 2012 Nov. 1; 186(9):897-908.
(27) Mair K M, MacLean M R, Morecroft I, Dempsie Y, Palmer™. Novel interactions between the 5-HT transporter, 5-HT(1B) receptors and Rho kinase in vivo and in pulmonary fibroblasts. *British Journal of Pharmacology* 2008 October; 155(4):606-16.
(28) Seuwen K, Magnaldo I, Pouyssegur J. Serotonin stimulates DNA synthesis in fibroblasts acting through 5-HT1B receptors coupled to a Gi-protein. *Nature* 1988 Sep. 15; 335(6187):254-6.

The invention claimed is:

1. A method for prophylaxis or treatment of pulmonary hypertension, comprising delivering to a target cell, or administering to a subject:
   (a) miR-96, a mimic thereof, or a precursor of either; or
   (b) a nucleic acid encoding miR-96, a mimic thereof, or a precursor of either.

2. A method for pulmonary vascular remodelling, comprising delivering to a target cell, or administering to a subject:
   (a) miR-96, a mimic thereof, or a precursor of either; or
   (b) a nucleic acid encoding miR-96, a mimic thereof, or a precursor of either.

3. A method according to claim 1 wherein said pulmonary hypertension is pulmonary arterial hypertension.

4. A method according to claim 1 wherein the target cell expresses the 5-HT1B receptor.

5. A method according to claim 1 wherein the target cell is a vascular cell.

6. A method according to claim 5 wherein the vascular cell is a vascular smooth muscle cell (VSMC) or a vascular endothelial cell.

7. A method according to claim 6 wherein the vascular cell is a pulmonary artery smooth muscle cell (PASMC) or pulmonary artery endothelial cell.

8. A method according to claim 1 wherein the target cell is a cell associated with the vasculature.

9. A method according to claim 8 wherein the target cell is an adventitial fibroblast or an immune cell.

10. A method according to claim 9 wherein the immune cell is a T lymphocyte, monocyte, macrophage or mast cell.

11. A method according to claim 1 wherein the precursor of miR-96 is pre-miR-96.

12. A method according to claim 11 wherein the pre-miR-96 has the sequence:

```
(hsa-pre-miR-96)                              (SEQ ID NO: 3)
UGGCCGAUUUUGGCACUAGCACAUUUUUGCUUGUGUCUCUCCGCUCUGAG
CAAUCAUGUGCAGUGCCAAUAUGGGAAA
or (mmu-pre-miR-96)                              (SEQ ID NO: 4)
CCAGUACCAUCUGCUUGGCCGAUUUUGGCACUAGCACAUUUUUGCUUGUG
UCUCUCCGCUGUGAGCAAUCAUGUGUAGUGCCAAUAUGGGAAAAGCGGGC
UGCUGC,
``` wherein the mature miR-96 sequence is underlined.

13. A method according to claim 1 wherein the precursor of miR-96 is pri-miR96.

14. A method according to claim 1 wherein the miR-96 mimic comprises a guide strand which has the sequence:

```
UUUGGCACUAGCACAUUUUUGCU           (SEQ ID NO: 1)
```

(wherein the seed sequence is underlined)
or which differs from that sequence at one or more positions outside the seed sequence.

15. A method according to claim 14 wherein the miR-96 mimic comprises:

(a) one or more modified sugar residues;
(b) one or more modified internucleoside linkages; or
(c) one or more modified bases.

16. A method according to claim 1 wherein the miR-96, mimic or precursor thereof is associated with a carrier, wherein the carrier is a pharmaceutically acceptable lipid or polymer, or a combination thereof.

17. A method according to claim 1 wherein the nucleic acid is delivered as naked DNA or in association with a carrier.

18. A method according to claim 1 wherein the nucleic acid is delivered via a viral vector.

19. A method according to claim 18 wherein the viral vector is an adenoviral or retroviral vector.

20. A method according to claim 19 wherein the retroviral vector is a lentiviral vector.

* * * * *